US009050269B2

(12) United States Patent
Discher et al.

(10) Patent No.: US 9,050,269 B2
(45) Date of Patent: Jun. 9, 2015

(54) PROTECTION OF VIRUS PARTICLES FROM PHAGOCYTOSIS BY EXPRESSION OF CD47

(75) Inventors: Dennis E. Discher, Philadelphia, PA (US); Richard Kuo-An Tsai, Boston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 584 days.

(21) Appl. No.: 12/721,287

(22) Filed: Mar. 10, 2010

(65) Prior Publication Data

US 2010/0316570 A1      Dec. 16, 2010

Related U.S. Application Data

(60) Provisional application No. 61/158,985, filed on Mar. 10, 2009.

(51) Int. Cl.

| | |
|---|---|
| *A61K 9/51* | (2006.01) |
| *C07K 14/705* | (2006.01) |
| *A61K 39/12* | (2006.01) |
| *A61K 47/48* | (2006.01) |
| *C12N 7/00* | (2006.01) |
| *A61K 48/00* | (2006.01) |
| *A61K 39/00* | (2006.01) |

(52) U.S. Cl.
CPC ............ *A61K 9/5184* (2013.01); *C07K 14/705* (2013.01); *A61K 35/13* (2013.01); *A61K 39/12* (2013.01); *A61K 47/48776* (2013.01); *A61K 48/00* (2013.01); *A61K 2039/5256* (2013.01); *C12N 7/00* (2013.01); *C12N 2740/15051* (2013.01)

(58) Field of Classification Search
CPC ............... A61K 9/5184; A61K 39/12; A61K 2039/5256; C12N 7/00
See application file for complete search history.

(56) References Cited

U.S. PATENT DOCUMENTS

| | | | | |
|---|---|---|---|---|
| 6,627,442 | B1 * | 9/2003 | Humeau et al. | 435/455 |
| 7,282,556 | B2 * | 10/2007 | Parkos | 530/327 |

OTHER PUBLICATIONS

Subramanian "Species- and cell type-specific interactions between CD47 and human SIRP" Blood, 107(6): 2548-2556, 2006.*
Greenberg "Targeted Transgene Expression in Müller Glia of Normal and Diseased Retinas Using Lentiviral Vectors" Investigative Ophthalmology & Visual Science, Apr. 2007, vol. 48, No. 4.*
Ramana, L. N., et al., 2014, Targeting strategies for delivery of anti-HIV drugs, J. Controlled Release, 192:271-283.*
Oliver, et al., "Rhinovirus exposure impairs immune responses to bacterial products in human alveolar macrophages," Thorax, 2008;63:519-525.
Oldenborg, et al., "Role of CD47 as a Marker of Self on Red Blood Cells," Science, Jun. 2000, 288:2051-2054.
Okazawa, et al., "Negative Regulation of Phagocytosis in Macrophages by the CD47-SHPS-1 System," The Journal of Immunology, 2005;174:2004-2011.
Arndt, et al., "$Rh_{null}$ red blood cells with reduced CD47 do not show increased interactions with peripheral blood monocytes," British Journal of Haematology, 2004;125:405-417.
Tsai, et al., "Inhibition of "self" engulfment through deactivation of myosin-II at the phagocytic synapse between human cells," JCB, vol. 180, Nov. 2008, pp. 989-1003.
Subramanian, et al., "Membrane mobility and clustering of Integrin Associated Protein (IAP, CD47)—Major differences between mouse and man and implications for signaling," Blood Cells, Molecules, and Diseases, 2006;36:364-372.
Moghimi, et al., "Long-Circulating and Target-Specific Nanoparticles: Theory to Practice," Pharmacological Reviews, 58:283-318, 2001.
Wright, et al., "Phagocytosing macrophages exclude proteins from the zones of contact with opsonized targets," Nature, vol. 309, May 1984, pp. 359-361.
Alcami, et al., "Viral mechanisms of immune evasion," Trends in Microbiology, 2000.
Ram, et al., "A Novel Sialic Acid Binding Site on Factor H Mediates Serum Resistance of Sialylated Neisseria gonorrhoeae," J. Exp. Med., vol. 187, No. 5, Mar. 1998, pp. 743-752.
Weiskopf, et al. "Engineered SIRPa Variants as Immunotherapeutic Adjuvants to Anticancer Antibodies" 2013, Science 341:88-91.
Weiskopf, et al. "Engineered SIRPa Variants as Immunotherapeutic Adjuvants to Anticancer Antibodies" 2013, Science, Supplementary Materials, 341:1-36.
Kershaw, et al., "Making Macrophages Eat Cancer." 2013, Science, 341:41-42.

* cited by examiner

Primary Examiner — Jeffrey Parkin
(74) Attorney, Agent, or Firm — Saul Ewing, LLP; Kathryn Doyle

(57) ABSTRACT

The present invention relates to a viral particle. The viral particle has a radius of less than about 1 μm, and at least one peptide comprising at least a biologically active portion of CD47. The present invention also includes a method of increasing the life of a particle in vivo in a mammal. The method includes the steps of expressing at least one peptide comprising at least a biologically active portion of CD47 in a viral particle, and administering the viral particle having CD47 expressed to a mammal, wherein the administered viral particle has a longer half life in the mammal than an otherwise identical viral particle that does not have CD47 expressed thereon.

14 Claims, 31 Drawing Sheets

A

B

PROTECTION OF VIRUS PARTICLES FROM PHAGOCYTOSIS BY EXPRESSION OF CD47

CROSS REFERENCE TO RELATED APPLICATION

This application claims priority under 35 U.S.C. §119(e) to U.S. Provisional Application No. 61/158,985, filed Mar. 10, 2009, which application is incorporated by reference herein in its entirety.

STATEMENT REGARDING FEDERALLY SPONSORED RESEARCH OR DEVELOPMENT

This invention was made with government support under Grant No. 2R01HL062352-09A1, awarded by the National Institutes of Health. The U.S. Government therefore has certain rights in this invention.

BACKGROUND OF THE INVENTION

The internalization of extracellular material into cells is commonly performed by a process called endocytosis (Rabinovitch, 1995, Trends Cell Biol. 5(3):85-7; Silverstein, 1995, Trends Cell Biol. 5(3):141-2; Swanson et al., 1995, Trends Cell Biol. 5(3):89-93; Allen et al., 1996, J. Exp. Med. 184(2):627-37). Endocytosis may fall into two general categories: phagocytosis, which involves the uptake of particles, and pinocytosis, which involves the uptake of fluid and solutes.

Phagocytosis is conducted primarily by highly specialized cells, such as macrophages, monocytes and neutrophils, with the goal of clearing pathogens and/or debris (Aderem et al., 1999, Annu. Rev. Immunol. 17:593-623; Stuart et al., 2008, Nat. Rev. Immunol. 8(2):131-41). Phagocytosis is an active and highly regulated process that is dependent on both actin (Wang et al., 1984, J. Cell Biol. 98(4):1328-41; Greenberg et al., 1990, J. Exp. Med. 172(6):1853-6) and myosin (Stendahl et al., 1980, J. Cell Biol. 84(2):215-24; Valerius et al., 1981, Cell 24(1):195-202; Diakonova et al., 2002, Mol. Biol. Cell 13(2):402-11), but is typically independent of clathrin (Aderem et al., 1999, Annu. Rev. Immunol. 17:593-623; Tse et al., 2003, J. Biol. Chem. 278(5):3331-8). Phagocytosis involves a highly efficient mechanism for internalizing foreign invaders and particles that the phagocytic cell recognizes through an array of receptors (Silverstein, 1995, Trends Cell Biol. 5(3):141-2). These specific cell-surface receptors recognize opsonin, including Fc receptors (FcR) on macrophages that are activated by antibodies bound to the targets (Greenberg et al., 1993, J. Exp. Med. 177(2):529-34; Ravetch, 1994, Cell 78(4):553-60). A number of cytoskeletal proteins have been specifically shown to be involved in FcR phagocytosis, such as myosins (Cox et al., 2002, Nat. Cell Biol. 4(7):469-77; Diakonova et al., 2002, Mol. Biol. Cell 13(2):402-11).

A phagocytic cell engulfs another cell or particle that is IgG-opsonized in a coordinated process of adhesion, pseudopod extension, and internalization with phagosome closure. Upon initial binding of IgG, the phagocyte's Fc receptors (FcγRs) activate cytoskeletal assembly with rapid accumulation of phosphopaxillin (Greenberg et al., 1994, J. Biol. Chem. 269(5):3897-3902; Allen et al., 1996, J. Exp. Med. 184(2):627-37) and F-actin (Wang et al., 1984, J. Cell Biol. 98(4):1328-41; Greenberg et al., 1991, J. Cell Biol. 113:757-767) among other components at a "phagocytic synapse." Non-muscle myosins also accumulate and suggest a role(s) for contractile motors during particle internalization (Stendahl et al., 1980, J. Cell Biol. 84(2):215-24; Valerius et al., 1981, Cell 24(1):195-202; Diakonova et al., 2002, Mol. Biol. Cell 13(2):402-11). Signaling activities that influence synapse assembly continue to be clarified (Aderem et al., 1999, Annu Rev. Immunol. 17:593-623) and are presumably key to how the macrophage distinguishes foreign cells or particles from autologous cells of "self." Autologous cells are believed to be opsonized by Ig (Turrini et al., 1993, Blood 81(11):3146-52), and so activation differences only tell a portion of the story.

In addition to activation, professional phagocytes have been shown to differentiate from non-self and self, based on studies with knockout mice lacking the membrane receptor CD47 (Oldenborg et al., 2000, Science 288(5473):2051-4). CD47 is a ubiquitous member of the Ig superfamily that interacts with the immune inhibitory receptor SIRPα (signal regulatory protein) found on macrophages (Fujioka et al., 1996, Mol. Cell. Biol. 16(12):6887-99; Veillette et al., 1998, J. Biol. Chem. 273(35):22719-28; Jiang et al., 1999, J. Biol. Chem. 274(2):559-62). Although CD47-SIRPα interactions appear to deactivate autologous macrophages in mouse, severe reductions of CD47 (perhaps 90%) are found on human blood cells from some Rh genotypes that show little to no evidence of anemia (Mouro-Chanteloup et al., 2003, Blood 101(1):338-344) and also little to no evidence of enhanced cell interactions with phagocytic monocytes (Arndt et al., 2004, Br. J. Haematol. 125(3):412-4). This interaction activates SHP-1 phosphatase (Tsuda et al., 1998, J. Biol. Chem. 273(21):13223-9; Veillette et al., 1998, J. Biol. Chem. 273(35):22719-28; Vernon-Wilson et al., 2000, Eur. J. Immunol. 30(8):2130-7; Kant et al., 2002, Blood 100(5):1852-1859) which leads to downstream targets such as non-muscle myosin IIA (NMMIIA) (Tsai et al., 2008, J. Cell Biol. 180 (5):989-1003).

Macrophages are proficient at discriminating between foreign cells or particles in the microbe size range. However, this self signal, CD47, is not understood in targets less than 500 nm in size. Particles that are in the nanometer length scales may undergo a different process from the traditional phagocytosis pathways (Wright et al., 1984, Nature 309(5966):359-61) which may include macropinocytosis (Koval et al., 1998, Exp. Cell. Res. 242(1):265-73; Rejman et al., 2004, Biochem. J. 377(Pt 1):159-69). Thus, macrophage targets using the CD47 self signal have not been shown in the nanoscale range, making the hypothesis of the viability of CD47 inhibition unknown at these smaller length scales.

Thus, there is a long felt need in the art for effective viral drug delivery vehicles that can effectively evade the phagocytic cell uptake of the immune system, thereby resulting in a reduction of an immune response. The present invention meets this need.

SUMMARY OF THE INVENTION

The present invention relates to a viral particle having a radius of less than about 1 μm, and including at least one peptide including at least a biologically active portion of CD47. In another embodiment, the viral particle has a radius of less than about 400 nm. In another embodiment, the viral particle has a radius of less than about 150 nm.

In another embodiment, the at least one peptide is expressed on an exposed surface of the viral particle.

In another embodiment, the viral particle includes a lipid coat. In another embodiment, the viral particle is a lentivirus. In another embodiment, the amount of the biologically active CD47 in the viral particle is between about 20 and about 250 molecules/μm². In another embodiment, the biologically active portion of CD47 is human CD47.

In another embodiment, the viral particle includes a therapeutic or diagnostic agent at least partially encapsulated or attached thereto. In a further embodiment, the agent is selected from the group consisting of organic compounds, inorganic compounds, hydrophobic pharmacological drugs, hydrophilic pharmacological drugs, radiopharmaceuticals, biologics, proteins, peptides, polysaccharides, nucleic acids, siRNA and RNAi.

The present invention also relates to a pharmaceutical composition including the aforementioned viral particle and a therapeutic or diagnostic agent, or a salt thereof, and a pharmaceutically acceptable carrier.

Figure 8:
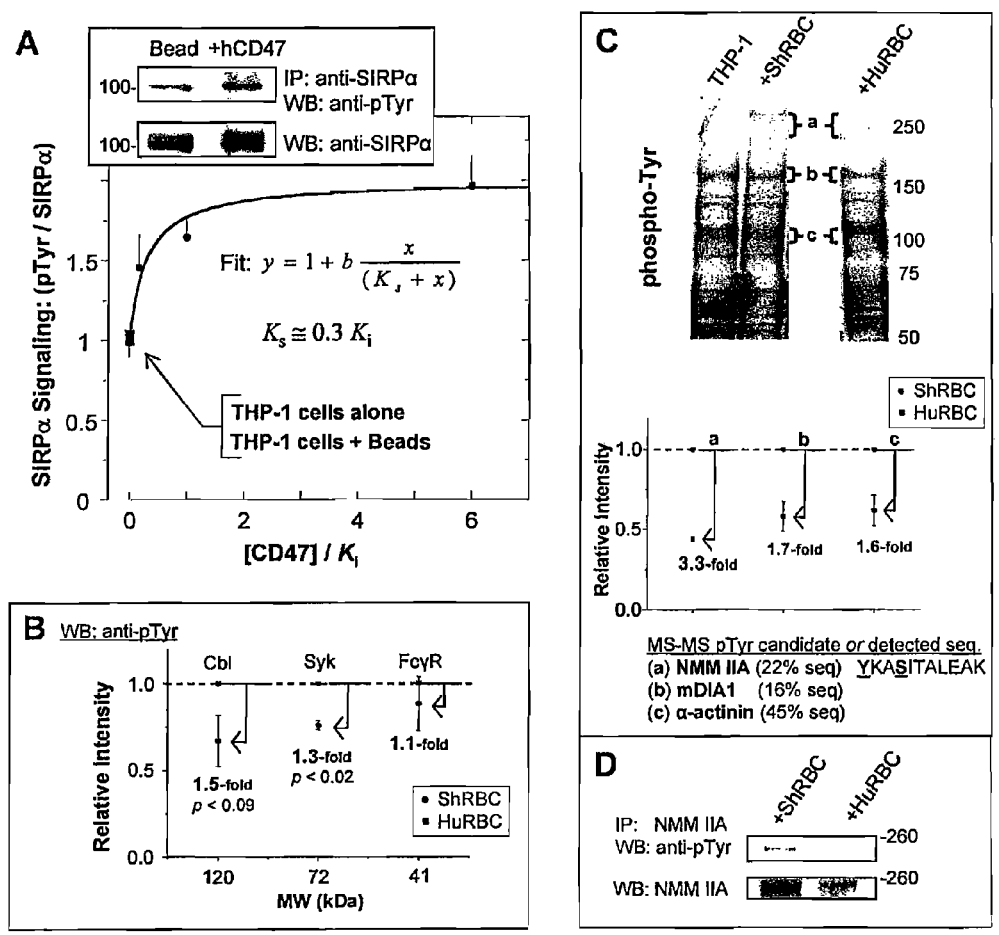

The present invention also relates to a method of evading phagocytosis of a particle by a phagocytic cell. The method includes expressing at least one peptide including at least a biologically active portion of CD47 in a viral particle so that, when the viral particle comprising the CD47 is exposed to a phagocytic cell, the viral particle evades phacocytosis by the phagocytic cell.

The present invention also relates to a method of increasing the life of a particle in vivo in a mammal. The method includes expressing at least one peptide including at least a biologically active portion of CD47 in a viral particle and administering the viral particle having CD47 expressed to a mammal, wherein the administered viral particle has a longer half life in the mammal than an otherwise identical viral particle that does not have CD47 expressed thereon.

The present invention also relates to a method of treating a medical condition in a subject in need of such treatment. The method comprises administering to the subject an effective amount of a therapeutic compound, or a salt thereof, in association with the aforementioned viral particle.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIGS. 1A-1B, illustrates species-specific binding of soluble human-SIRPα to RBCs and CD47-coated beads. FIG. 1A depicts fresh human and sheep RBC binding to soluble hSIRPα (4 μM of GST conjugate), as detected by FITC-anti-GST. 'Bkgd' is obtained with RBC plus antibody. FIG. 1B depicts affinity of hCD47-coated beads binding to soluble hSIRPα based on flow cytometry. The inset depicts inhibition of soluble hSIRPα binding to hCD47-beads by using anti-CD47 $F(ab)_2$ generated from B6H12 antibody; similar inhibition is obtained with human-RBC.

FIG. 2, comprising FIGS. 2A-2D, illustrates that signaling and cytoskeletal proteins at the Phagocytic Synapse depend on CD47. In FIGS. 2A and 2B, cells were stained for SIRPα and pTyr, and in FIGS. 2C and 2D, cells were stained for F-actin and non-muscle myosin IIA. Phagocytic synapses are indicated with black arrowheads in DIC images, and in fluorescence images with either white or gray arrowheads, depending on enrichment. The scale bars are 10 μm. Protein localization was quantified for phagocytic synapses randomly selected in DIC images (n=5, ±SD).

FIG. 3, comprising FIGS. 3A-3C, illustrates time lapse images of phagocytic synapse formation. Human-derived THP-1 macrophages were stably transfected with GFP-NMM IIA and incubated at 37° C. with IgG-opsonized sheep-RBC in FIG. 3A, or human-RBC for 10 min after an initial 4° C. incubation, in FIG. 3B. Time lapse images in DIC and fluorescence were taken upon identification of a target cell adhered to the macrophage. Arrows indicate the site of target cell contact with magnified images of the phagocytic synapse. The scale bars are 10 μm. FIG. 3C depicts phagocytic synapses fixed after 10 minutes. Cells were immunostained for total NMM IIA and protein localization to the phagocytic synapse was quantified for randomly chosen GFP+ cells by normalization to cytoplasmic intensity of 1.0 (n=5, ±SD).

FIG. 4, comprising FIGS. 4A-4B, illustrates CD47 inhibiting myosin localization as similar to blebbistatin. Phagocytic synapses of THP-1 macrophages with IgG-opsoninized sheep- or human-RBC (37° C., 10 min) after pre-incubation with blebbistatin (50 μM, 10 min). DMSO was used as a control. FIG. 4A depicts cells fixed and immunostained for non-muscle myosin IIA, F-actin, and Paxillin-$Y^{118}$. The scale bars are 10 μM. FIG. 4B depicts quantitation of protein localization to the phagocytic synapse relative to the cytoplasmic intensity set at 1.0 (n=5 cells, ±SD).

FIG. 5, comprising FIGS. 5A-5D, illustrates that human macrophages and monocytes are inhibited by human-CD47. FIG. 5A depicts DIC images of THP-1 phagocytes plus CD47-blocked, IgG-opsonized human-RBC, using $F(ab')_2$ made from monoclonal B6H12. The scale bars are 10 mm. FIG. 5B depicts human peripheral blood monocyte plus CD47-blocked human-RBC following lysis after 45 min of phagocytosis. PKH26 labeled human RBC are depicted in the right hand panel. Lysed RBC labeled with FITC-anti-Fc indicates the cell is not internalized. Human-RBC and Sheep-RBC were phagocytosed by THP-1 cells in FIG. 5C, or human monocytes in FIG. 5D, depicting phagocytosis increases with opsonization. Inset depicts blebbistatin treatment of ShRBC showing decrease in phagocytosis. Phagocytosis is measured as the ratio of internalized RBCs per phagocyte with 200 phagocytes counted in triplicate experiments (±SEM).

FIG. 6, comprising FIGS. 6A-6C, illustrates that human-CD47 is sufficient to inhibit phagocytosis. FIG. 6A depicts streptavidin beads coated with both anti-streptavidin IgG as the opsonin and biotinylated human-CD47. Phagocytosis of beads by THP-1 cells was assessed in DIC and fluorescence with non-ingested beads visible with rabbit anti-streptavidin plus a second, goat anti-rabbit antibody. The scale bars are 10 μm. Beads ±hCD47 (at normal RBC density) were engulfed by (B) THP-1 cells or human monocytes, demonstrating inhibition of phagocytosis by hCD47 unless the beads are blocked with anti-CD47. Inset bar graph compares to inhibited phagocytosis of uncoated beads after 10 min pretreatment of THP-1 cells with blebbistatin (50 μM). FIG. 6C depicts inhibition of phagocytosis depends on density of human-CD47 on beads. FIG. 6D depicts a bar graph comparing hCD47 inhibition of phagocytosis in peripheral blood monocytes.

FIG. 7 illustrates that myosin increases the efficiency of phagocytosis. Phagocytosis of IgG-opsoninized sheep-RBC was measured as a ratio of internalized RBCs per phagocyte with 200 phagocytes counted in triplicate experiments (±SEM). The level of NMM IIA activity is normalized to WT levels in THP-1, with relative levels of knockdown or overexpression quantified by immunofluorescence and Western blot. Results for phagocytosis of the IgG-opsoninzed sheep-RBC were fit to a line; where the intercept approximates the result for human-RBC. The inset bar graph depicts blebbistatin inhibition of ShRBC phagocytosis by GFP-NMMIIA expressing WT THP-1.

FIG. 8, comprising FIGS. 8A-8D, illustrates species-specific signaling through SIRPα and ultimately to cytoskeletal proteins. FIG. 8A depicts hCD47 or mCD47 were bound at varying densities to opsonized beads and phagocytosed by THP-1 macrophages. From macrophage lysates, SIRPα was immunoprecipitated and immunoblotted (inset) for quantitation of phospho-Tyr and total SIRPα for normalization. Fits of the data gave an effective signaling constant $K_s$ for each species that depends on the CD47 density; all densities are scaled by hCD47's inhibitory constant (K) as determined in FIG. 6 at the same opsonization. FIG. 8B depicts phosphotyrosine decreases in Cbl, Syk, and FcgR within THP-1 during phagocytosis of IgG-opsoninized human-RBC normalized to sheep-RBC. Whole cell lysates were immunoblotted and densitometry was used to quantify suitable MW bands. FIG. 8C depicts major phospho-tyrosine differences in THP-1 during phagocytosis of IgG-opsoninized human-RBC versus sheep-RBC. Whole cell lysates were immunoblotted and densitometry was used to identify bands (a,b,c) that showed the largest relative differences in intensity for sheep or human RBC targets compared to THP-1 cells. For bands a-c, the plot depicts the intensity obtained with phagocytosis of human-RBC relative to sheep-RBC (triplicate experiments±SEM). The list from MS analyses of bands a-c indicates top candidate phospho-proteins or else a directly detected sequence (for myosin). FIG. 8D depicts immunoprecipitation of NMM IIA from lysates followed by immunoblot for pTyr, confirming the major decrease in phospho-Tyr NMM IIA when THP-1 phagocytose human-RBC is compared to sheep-RBC.

Figure 9:
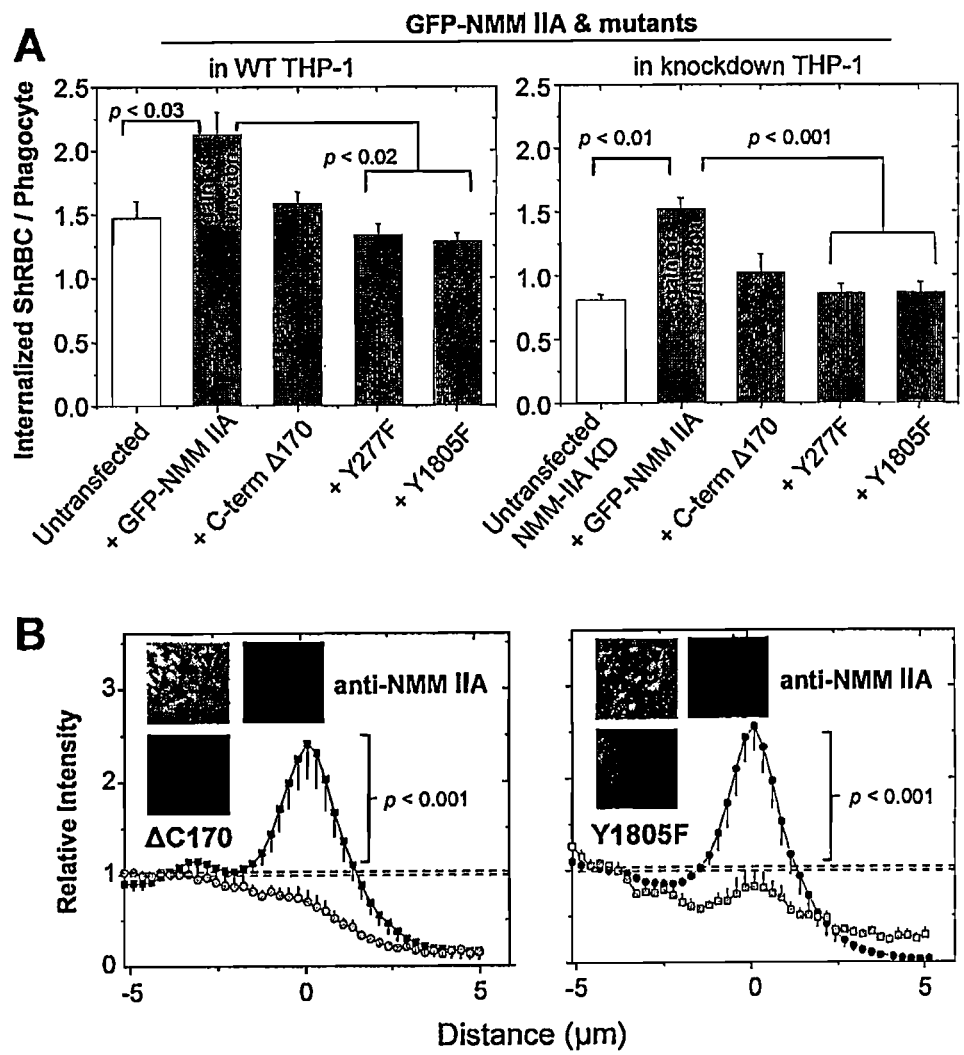

FIG. 9, comprising FIGS. 9A-9B, illustrates that phosphorylated myosin IIA is important for efficient phagocytosis. THP-1 macrophages and NMM-IIA knockdown THP-1 were used as is or else transfected with GFP-NMM IIA, GFP-ΔC170, GFP-Y277F, or GFP-Y1805F. FIG. 9A depicts phagocytosis of IgG-opsoninized sheep-RBC at 37° C. for 45 minutes, measured as the ratio of internalized RBCs per phagocyte with 200 phagocytes counted in triplicate experiments (±SEM). FIG. 9B depicts phagocytic synapses fixed after 10 min. Cells were stained for NMM IIA and protein localization to the phagocytic synapse was quantified for randomly chosen GFP+ cells by normalization to cytoplasmic intensity of 1.0 (n=5, ±SD).

Figure 10:
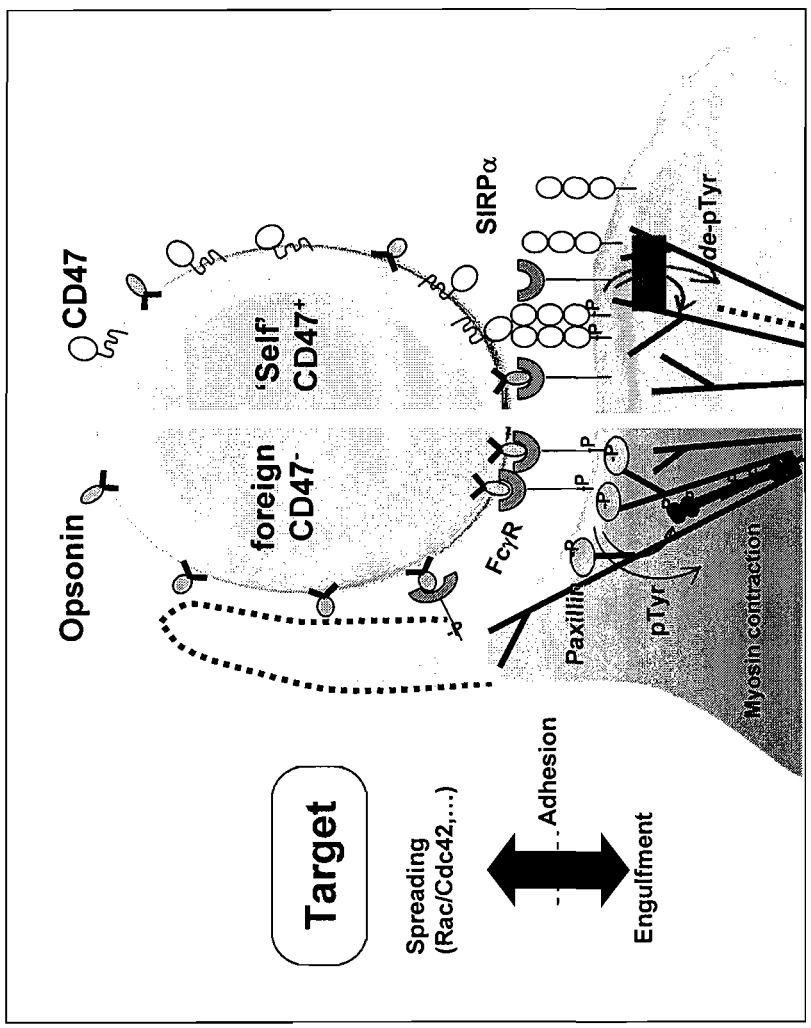

FIG. 10 illustrates phagocytic synapse and CD47's signaling in cytoskeleton remodeling. IgG-opsoninized target cell or particle lacking CD47 results binds FcgR, which activates assembly of paxillin, F-actin, and non-muscle myosin IIA at the synapse. In contrast, parallel interactions with CD47, signals through SIRPα to inhibit myosin assembly and contractile contributions to efficient phagocytosis.

Figure 11A:
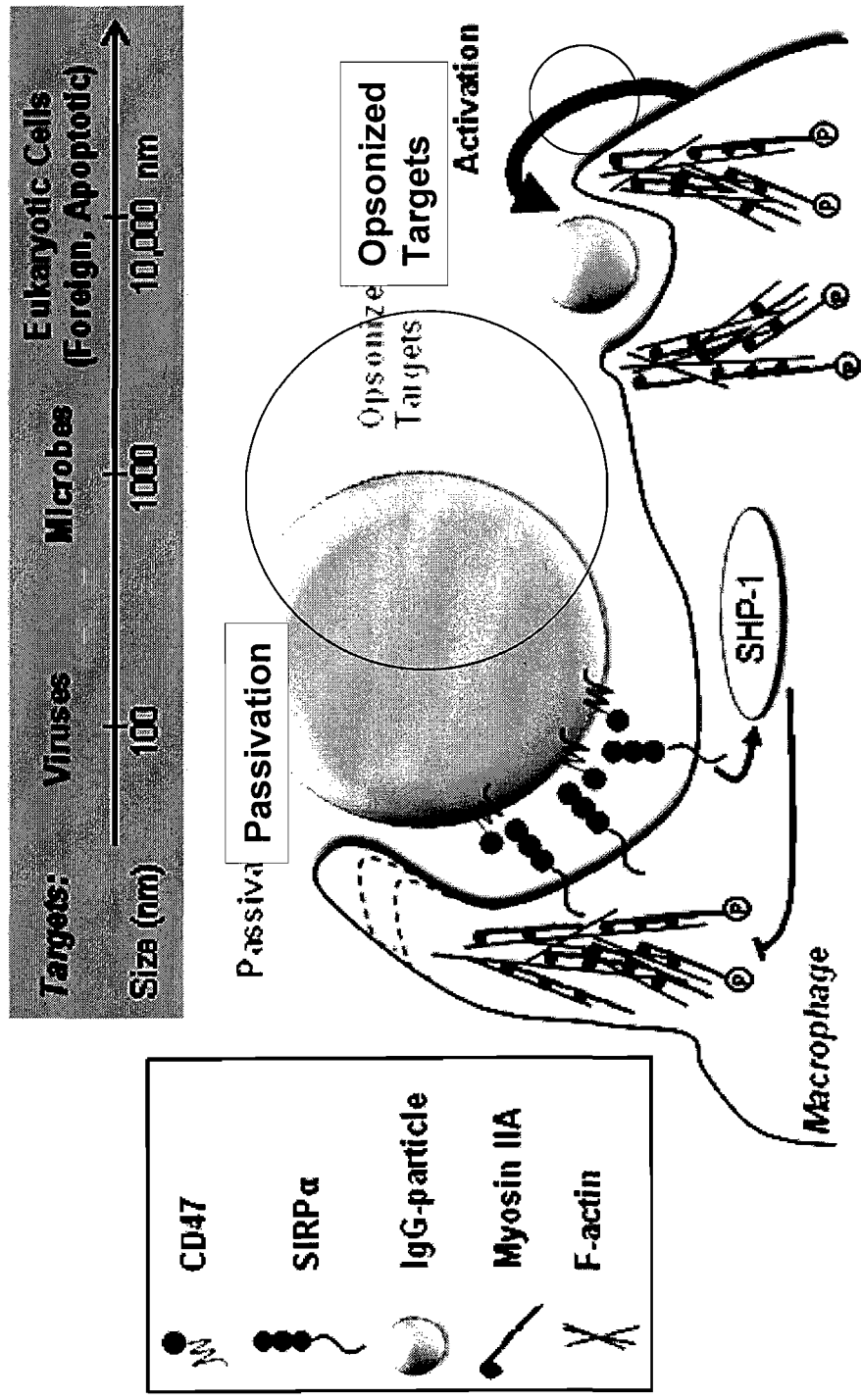
Figures 11B, 11C:
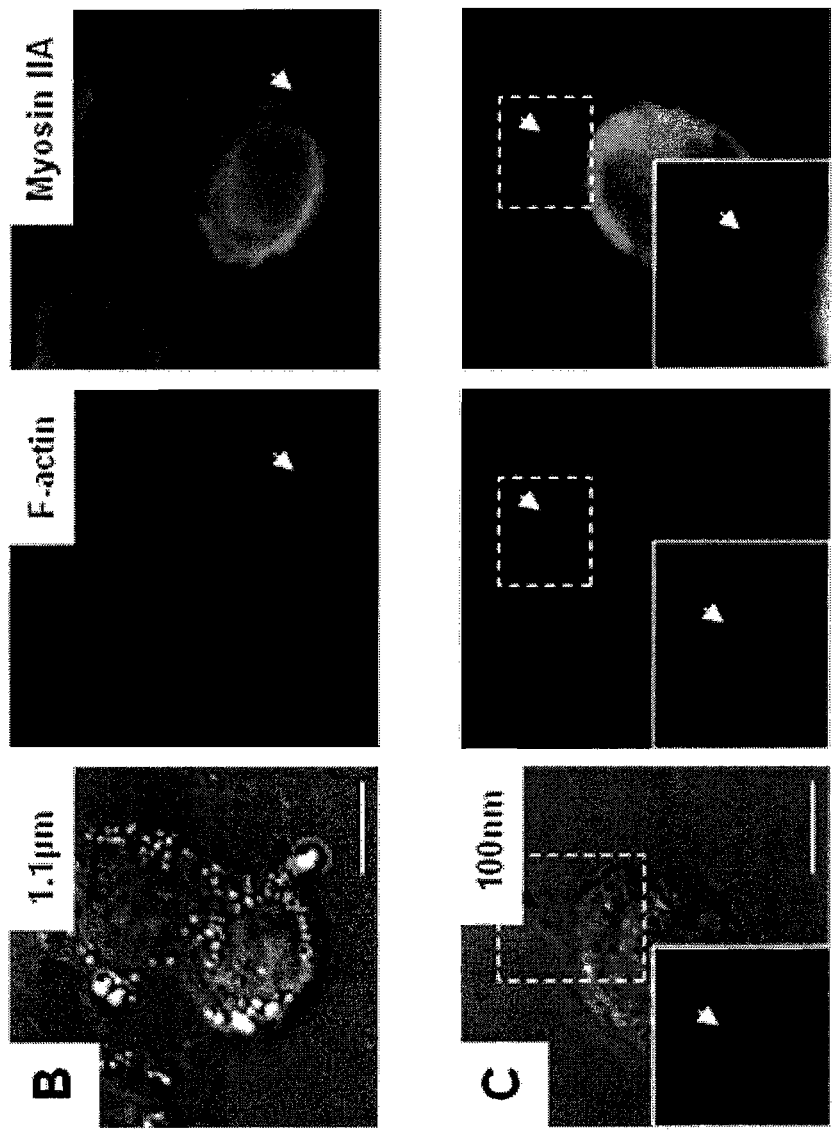
Figures 11D, 11E:
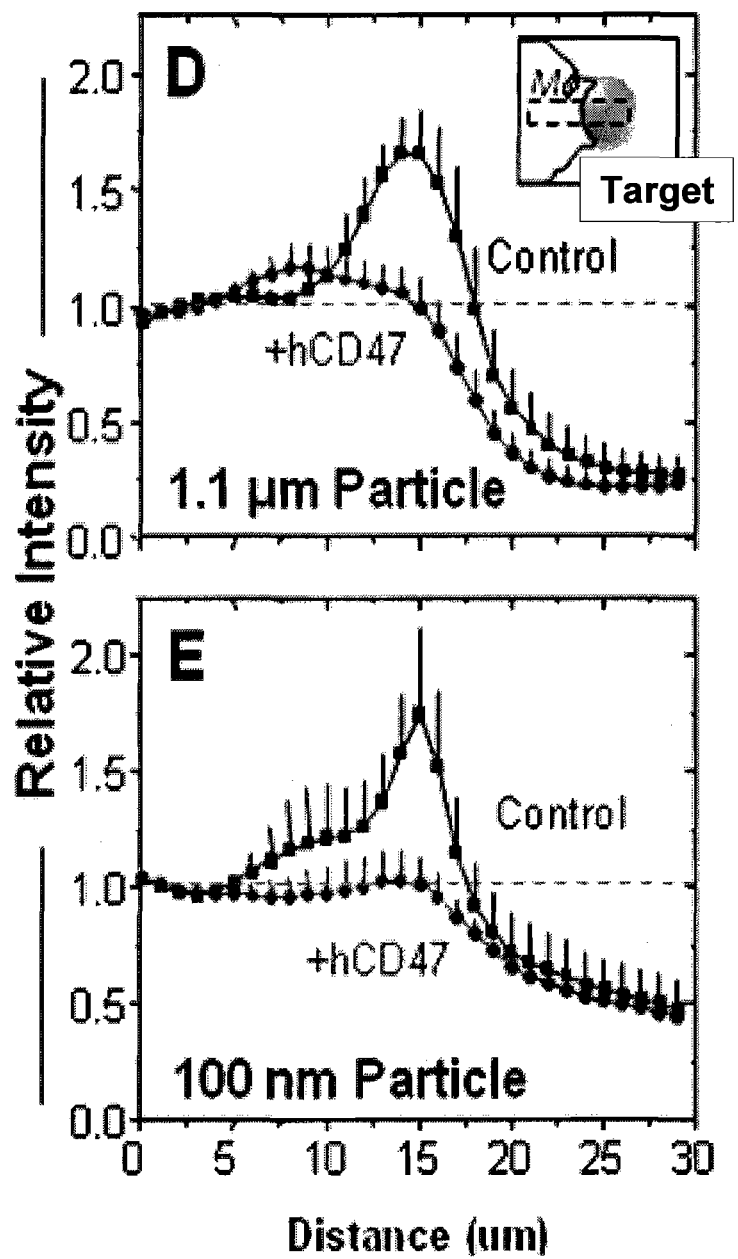

FIG. 11, comprising FIGS. 11A-11E, illustrates a model of phagocytosis and CD47's signaling in conserved cytoskeleton remodeling. FIG. 11A depicts IgG-opsonized targets from micro to nano sized particles lacking CD47 results in uptake, leading to the activation of F-actin, and non-muscle myosin IIA. In contrast, particles with CD47 signaling through SIRPα leads to the inhibition of myosin IIA, that leads to passivation. FIG. 11B depicts human-derived THP-1 macrophage IgG-opsonized at 1.1 μm. FIG. 11C depicts 100 nm streptavidin particle targets with F-actin and non-muscle myosin IIA after fixation of cells. Phagocytic synapses are indicated with black arrowheads in DIC images, and in fluorescence images with white arrowheads. Insets are magnified images of larger pictures depicted by dashed boxes. The scale bars are 10 μm. Protein localization for 1.1 μm particle (FIG. 11D) and for 100 nm particle (FIG. 11E) targets was quantified at the phagocytic synapses of random images and normalized to cytoplasmic intensity of 1.0 (n≥5, ±SD).

Figure 12:
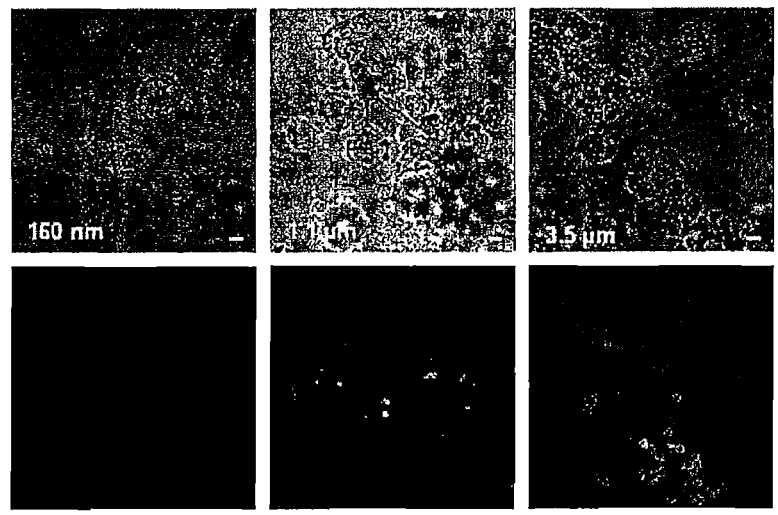
Figure 12:
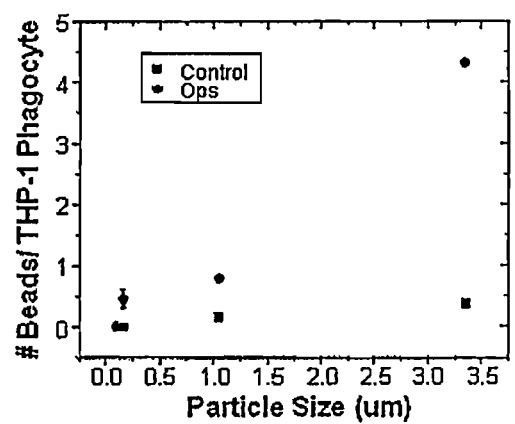

FIG. 12, comprising FIGS. 12A-12B, illustrates the effect of nano to micron sized particles in phagocytosis based mole ratio. FIG. 12A depicts nano to micron sized IgG particles in phase contrast images on top and fluorescent microscopy to determine phagocytosed versus non-phagocytosed. FIG. 12B depicts phagocytosis of IgG-opsonized beads (circles) and non IgG-opsonized controls (squares) was measured as a ratio of internalized RBCs per phagocyte, with 200 phagocytes counted (n=3, ±SD). The ratio of particle targets to THP-1 phagocytes was kept at a ratio of 20:1. Scale bar 10 μm.

Figure 13A:
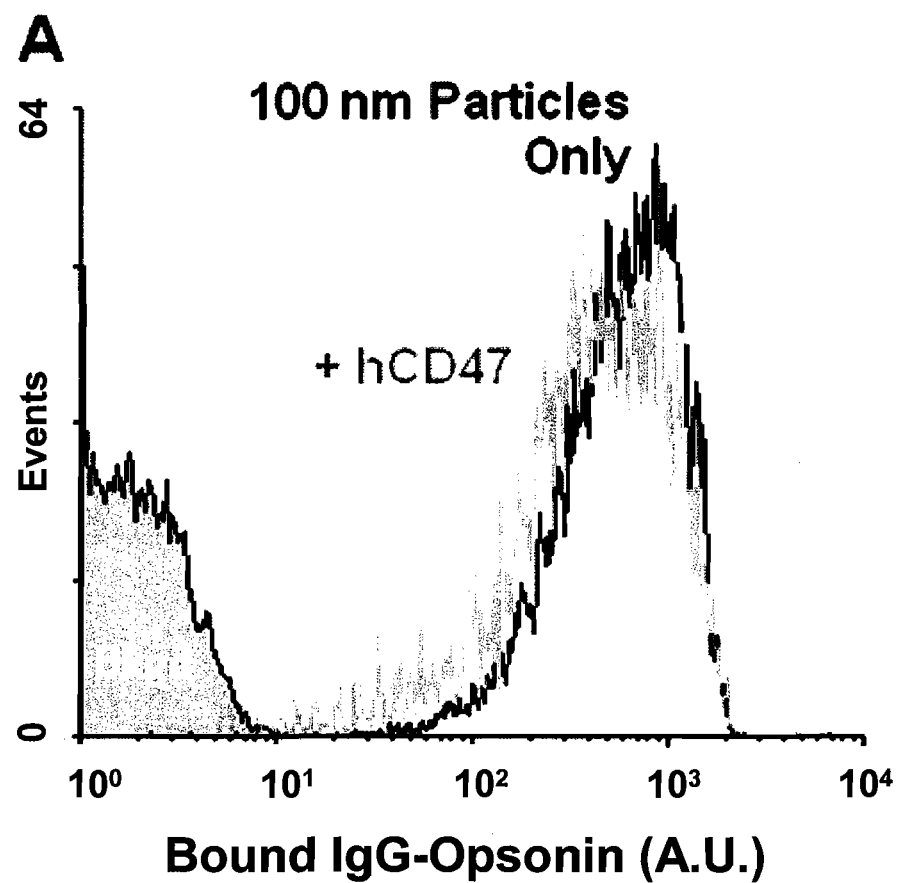
Figure 13B:
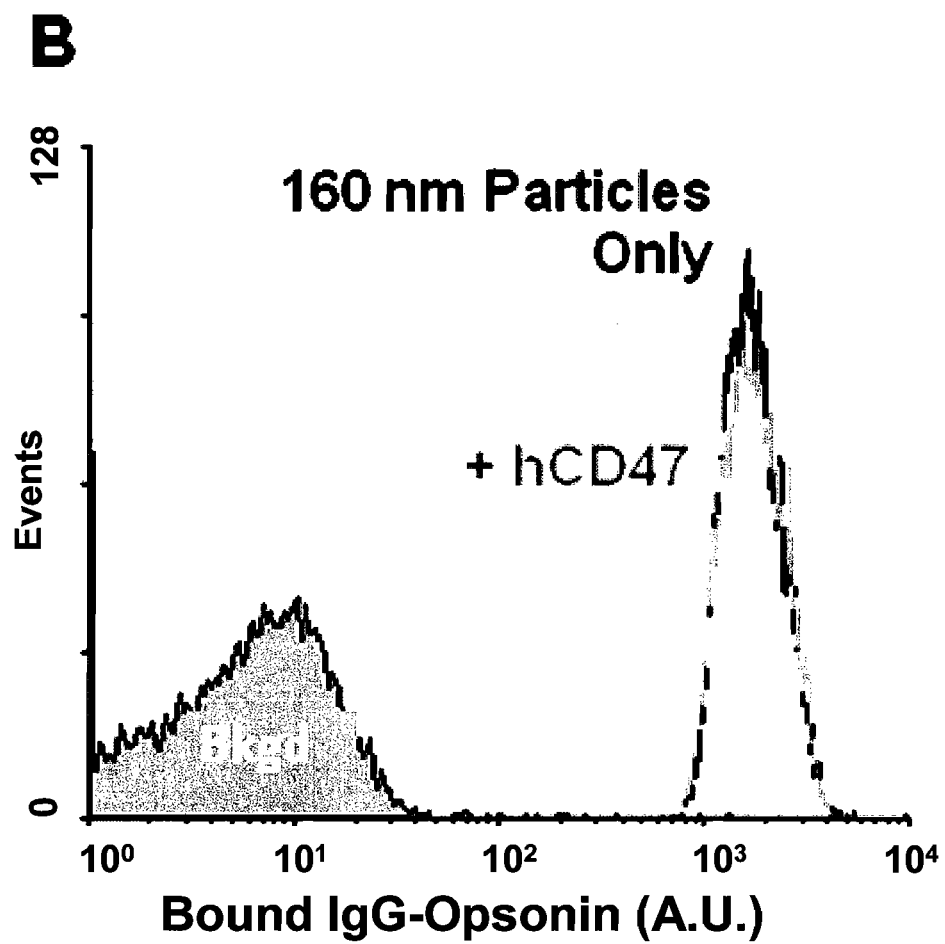
Figure 13C:
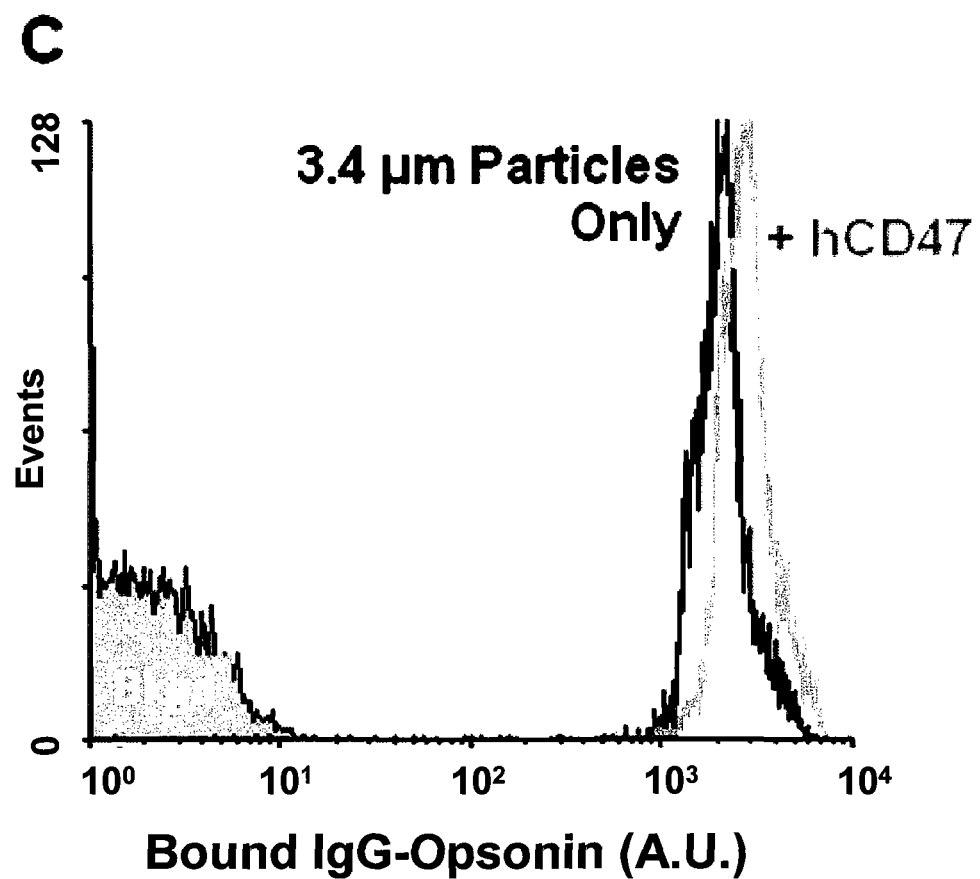

FIG. 13, comprising FIGS. 13A-13C, illustrates micro and nano-particle characterization. CD47 and IgG-opsonin non-competitive binding for CD47 coupled particles at normal physiological density (~250 molecules/μm$^2$) were IgG-opsonized and compared to particles alone (black) via FACS for 100 nm particles (FIG. 13A), 160 nm particles (FIG. 13B) and 3.4 μm particles (FIG. 13C).

Figure 14:
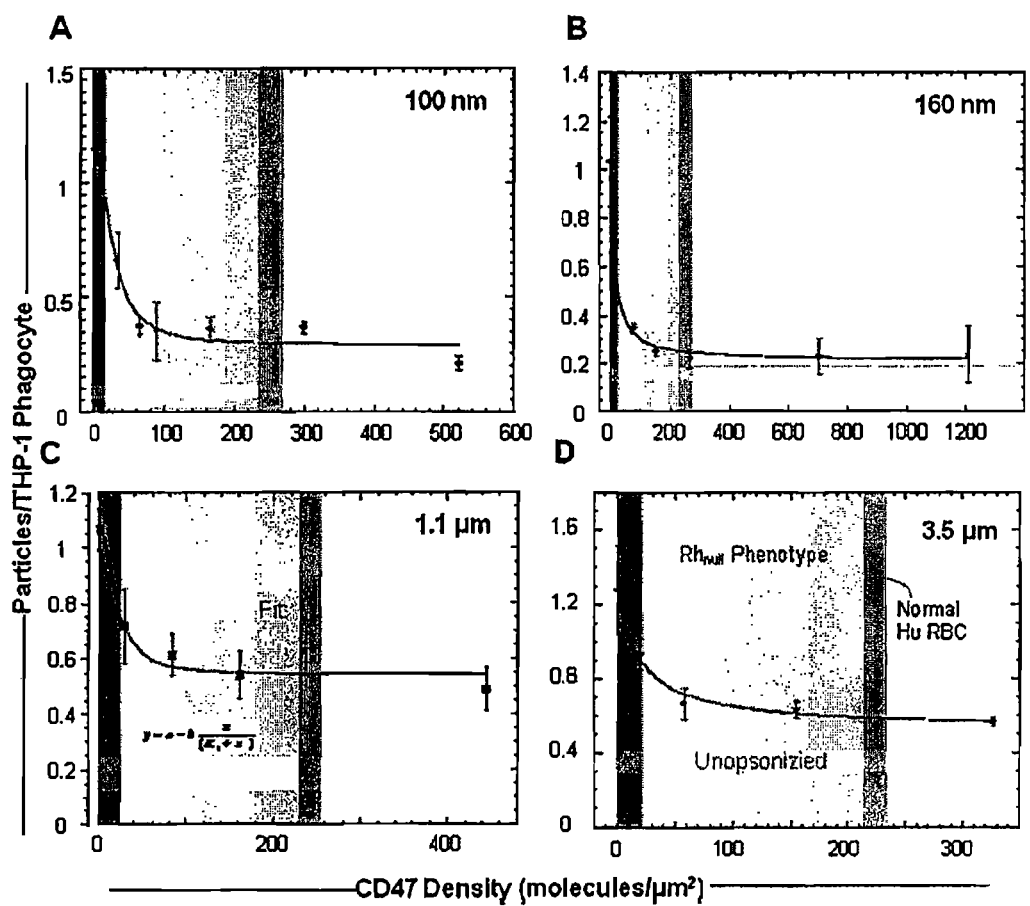

FIG. 14, comprising FIGS. 14A-14D, illustrates that CD47 inhibition of phagocytosis is potent from micro to nano scale particles. Streptavidin beads were coated with both anti-streptavidin IgG as the opsonin and biotinylated human CD47. Inhibition of phagocytosis is dependent on the density of human CD47 on beads having diameters of approximately 3.5 μm (FIG. 14A), 1.1 μm (FIG. 14B), 160 nm (FIG. 14C) and 100 nm (FIG. 14D). Phagocytosis inhibition occurs with an effective $K_i$~20 molecules/μm$^2$ for particles from micro to nano-meter beads and indicated by the transition period. The vertical bar is the normal density of CD47 found on human RBC (~250 CD47/μm$^2$) and the horizontal bar indicates the level of phagocytosis of unopsonized beads.

Figure 15A:
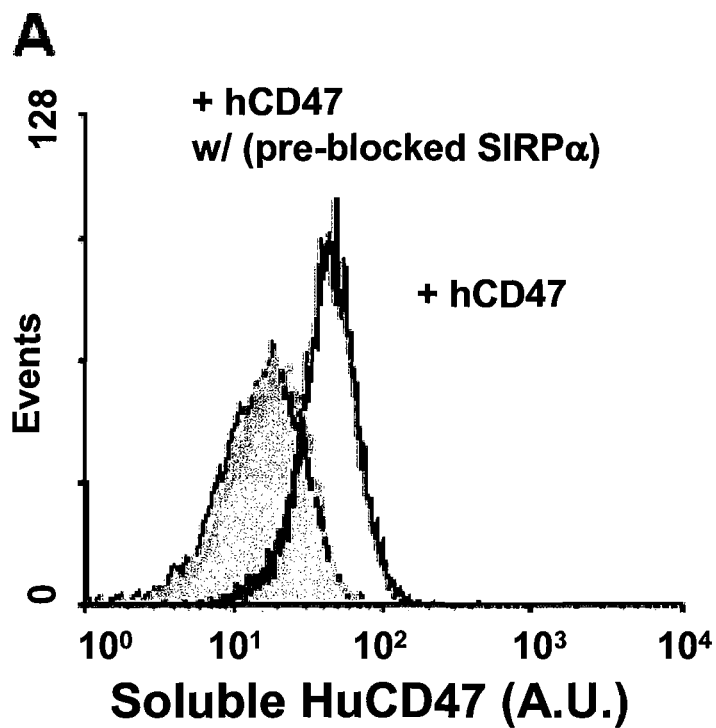
Figure 15B:
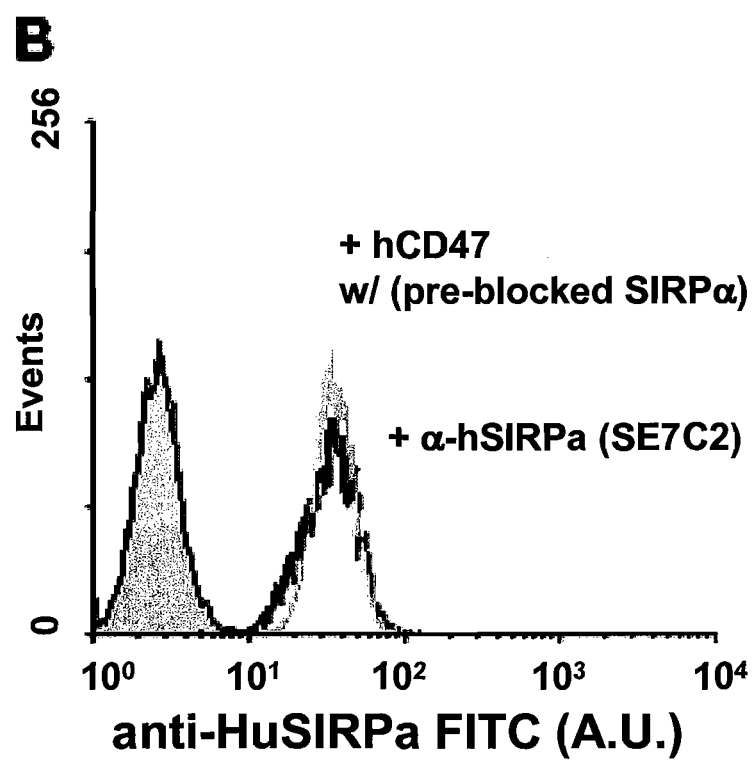

FIG. 15, comprising FIGS. 15A-15B, illustrates CD47 interacting specifically with SIRPα on THP-1 macrophages. HuCD47 binds specifically to SIRPα on THP-1 macrophages shown by FACS. FIG. 15A depicts soluble hCD47 (4 μM) binding with SIRPα on macrophages (black), but hCD47 no longer bound when SIRPα on THP-1 was pre-blocked with α-SIRPα (SE7C2) eliminating CD47-SIRPα binding. As illustrated in FIG. 15B, both pre-blocked SIRPα with soluble hCD47 and α-SIRPα (SE7C2) showed identical binding. Gray shade region is the background controls with secondary alone.

FIG. 16, comprising FIG. 16A-16D, illustrates CD47-SIRPα signaling pathway from SHP-1 to myosin. Phagocytosis of IgG-opsoninized particles with or without human CD47 of 100 nm particles (FIG. 16A) and 1.1 μm particles (FIG. 16B) were treated with an SHP-1 inhibitor (NSC-87877) at 62.5 nM and its effects were determined by the ratio of ingested particles per THP-1 phagocyte. The number of particles ingested was shown based on 200 phagocytes counted (n≥3, ±SD). The inset depicts the concentration dependence of NSC-87877 effect on particle uptake. Treatment of blebbistatin in THP-1 macrophages during phagocytosis of IgG-opsonizied 100 nm particles (FIG. 16C) and 1.1 μm particles (FIG. 16D) depict inhibition of phagocytosis. Human CD47 coated 100 nm particles show comparable levels to blebbistatin treated THP-1 phagocytes (n≥3, ±SD).

Figure 17A:
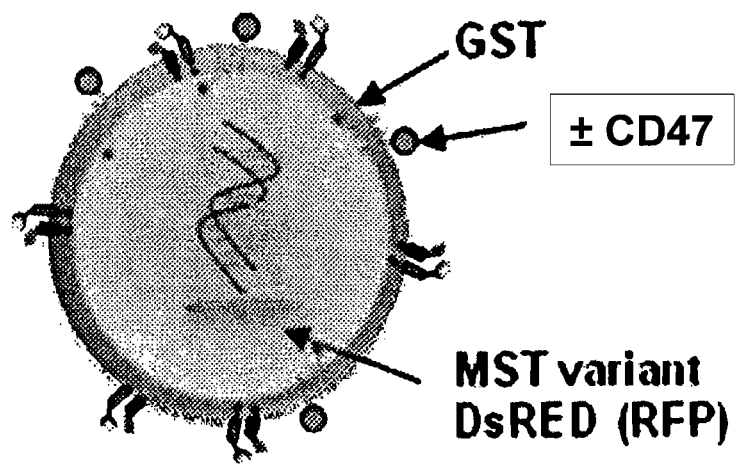
Figure 17A:
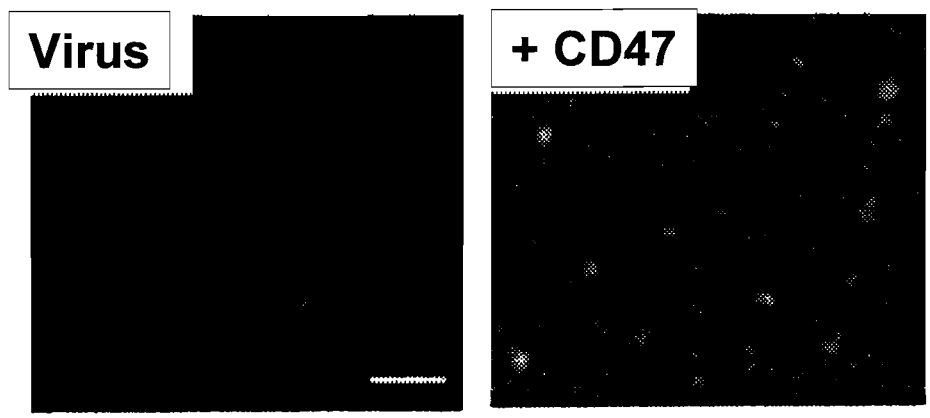
Figure 17B:
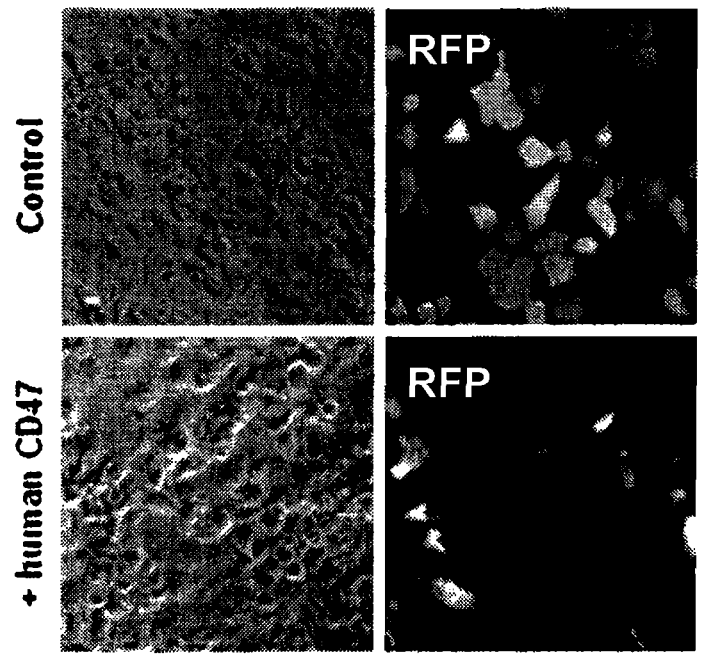
Figure 17D:
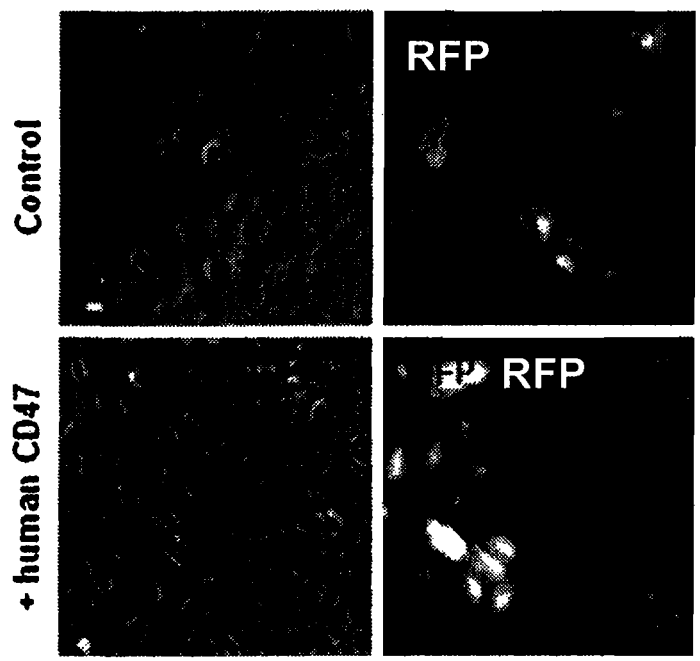
Figure 17C:
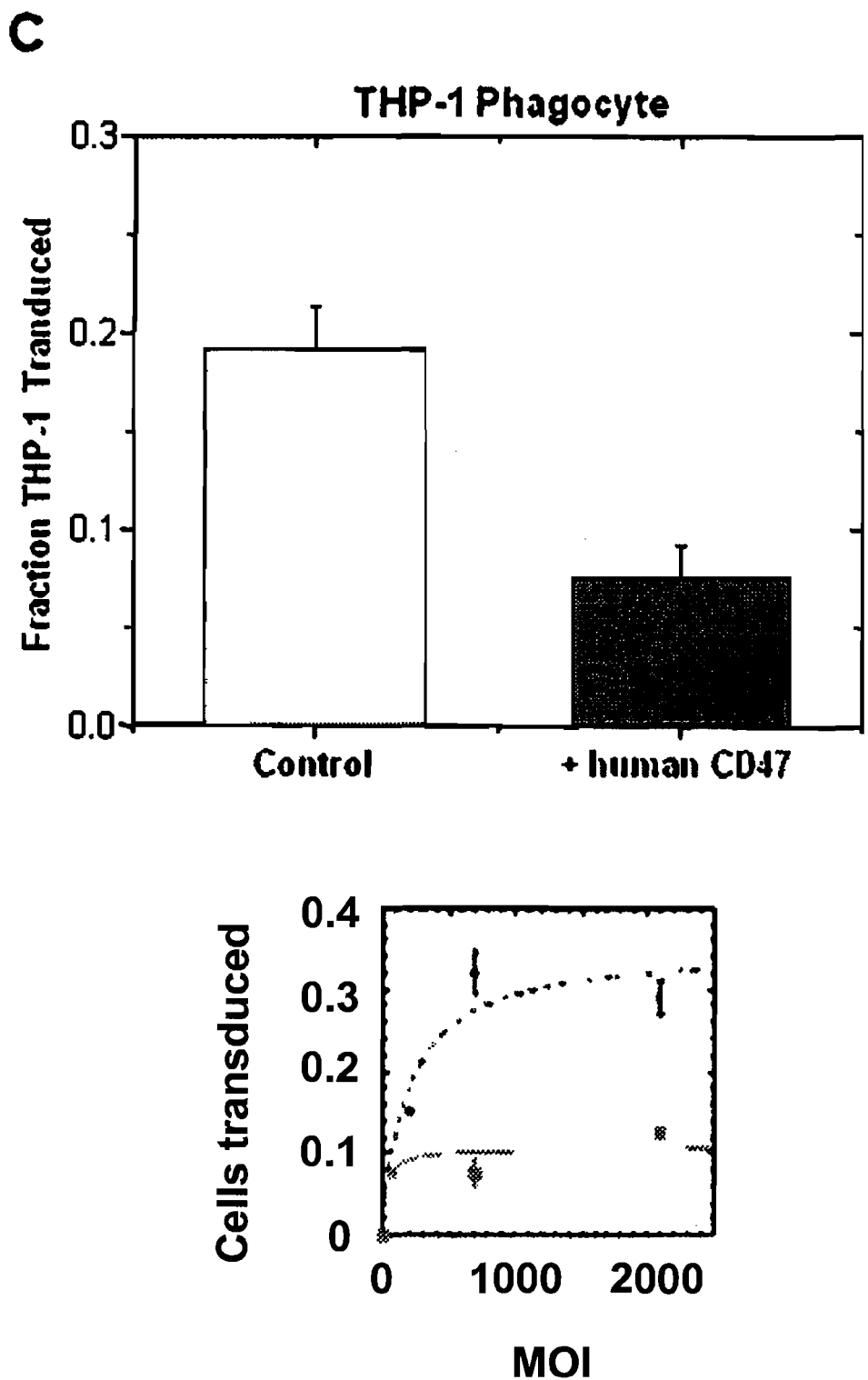
Figure 17E:
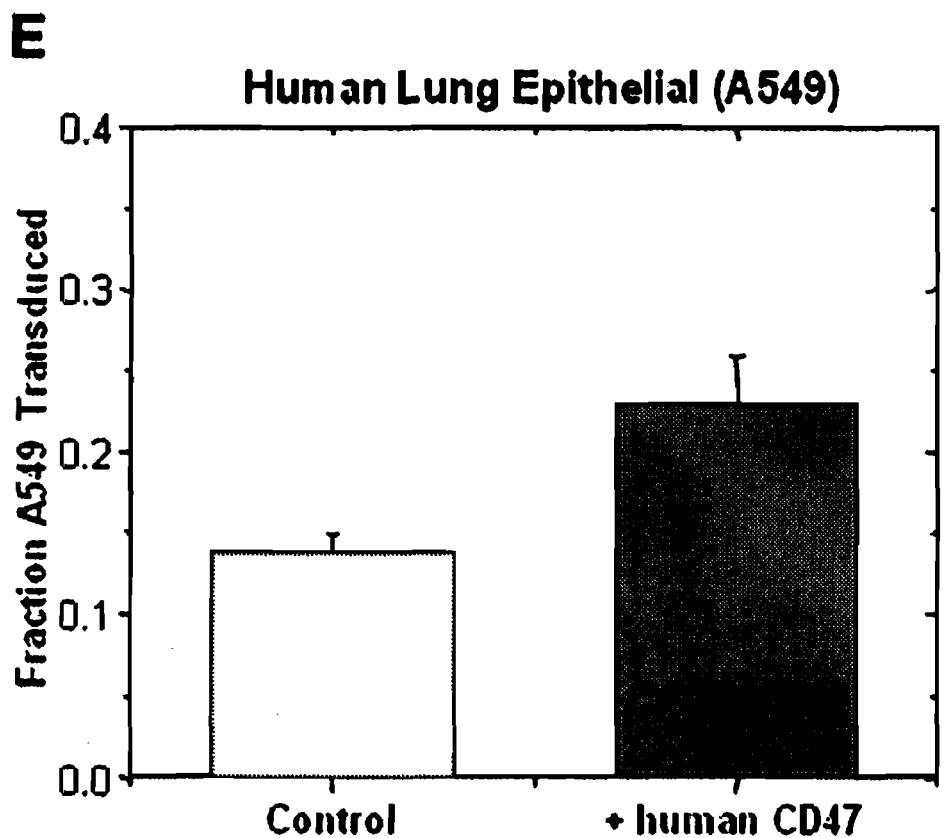
Figure 17E:
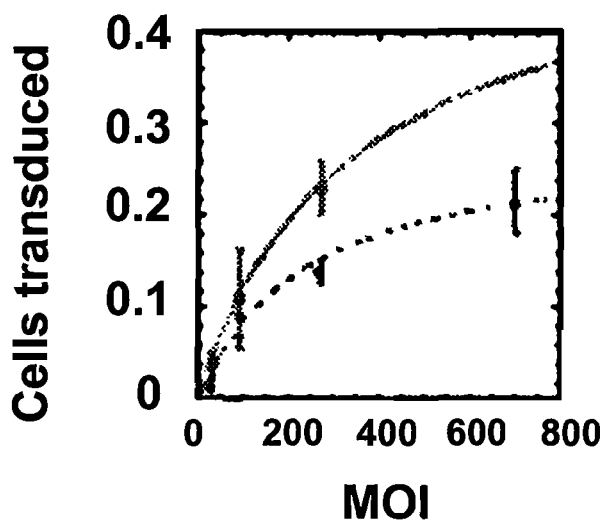

FIG. 17, comprising FIGS. 17A-17E, illustrates human CD47 lentivirus with a lower transduction rate of THP-1 macrophages. FIG. 17A depicts lentivirus particles containing MST variant of DsRed as readout of transduction and particles with or without full-length CD47 with GFP at the C-terminus. Lentivirus expression and hCD47 lentivirus co-localization are visible by fluorescent microscopy. The bars are 10 μm. The efficiency of lentiviral particle transduction was observed post-72 hours after infection (1 hr. at 37° C.) through RFP expression levels for THP-1 human macrophages (FIG. 17B) and A549 human alveolar epithelial cells (FIG. 17D). The top sets of images for each cell were using control lentiviral particles and the bottom are from lentiviral particles expressing human CD47. The scale bar is 10 μm. FIGS. 17 C and 17E depict the quantified results with 200 cells counted and repeated in triplicate (±SD). Insets of FIGS. 17C and 17E depict the effect of MOI in relation to transduction of cells for both control and overexpressed hCD47 lentivirus particles.

Figure 18:
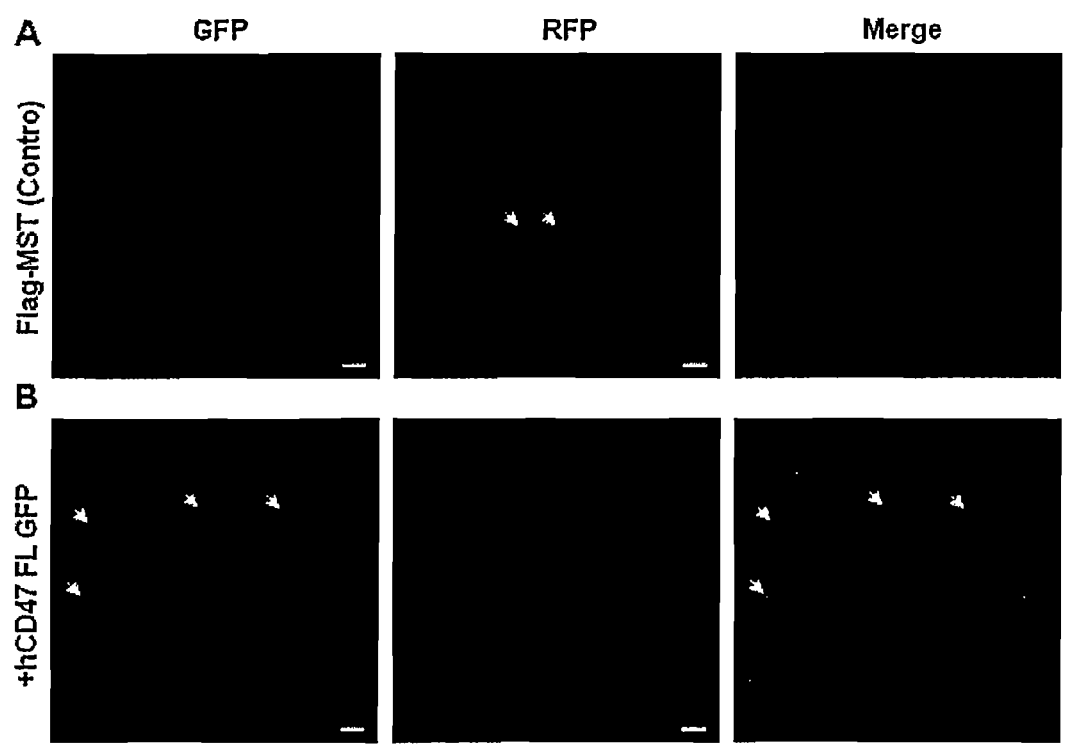

FIG. 18, comprising FIGS. 18A-18B, illustrates lentivirus characterization. Fluorescent microscopy images of lentivirus particles control with a flag-MST (FIG. 18A) in the RFP channel and full length human CD47 GFP virus (FIG. 18B). Merged images depict co-localization of virus and HuCD47 expression. The scale bar is 10 μm.

Figure 19:
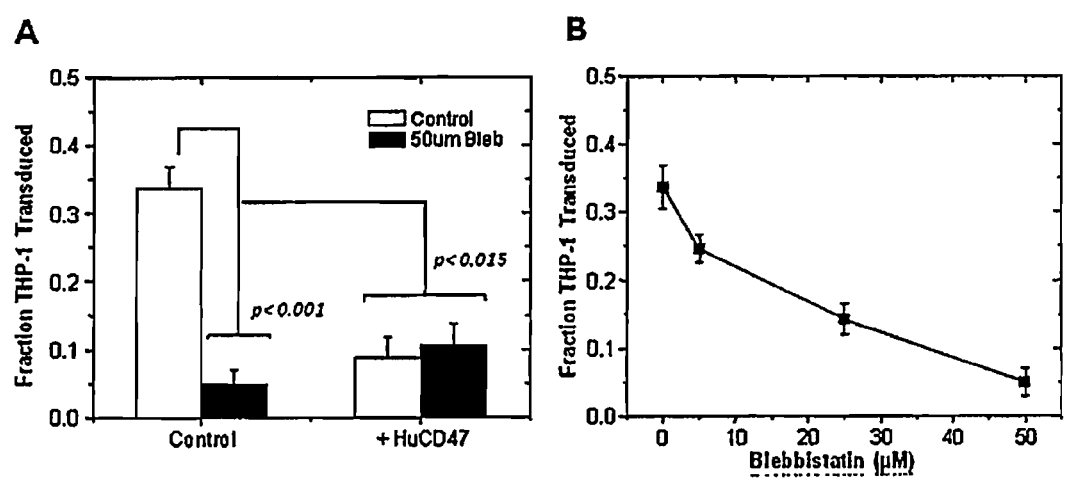

FIG. 19, comprising FIGS. 19A-19B, illustrates that lentiviral transduction is effected by myosin inhibition. Transduction of lentiviral particles was measured as a ratio of RFP expression per THP-1 phagocyte post-72 hours after initial infection (1 hr. at 37° C.) with greater than 200 phagocytes counted (n=3, ±SD). FIG. 19A depicts THP-1 phagocytes treated with DMSO (control) or 50 μM Blebbistatin (dark bars) for control lentiviral particles or lenti virus expressing human CD47 (HuCD47). FIG. 19B depict s blebbistatin treated THP-1 cells at various concentrated was infected with lentivirus at an MOI of 700. Infection was quantified by RFP expression by fluorescent microscopy. (n≥3, ±SD).

Figure 20:
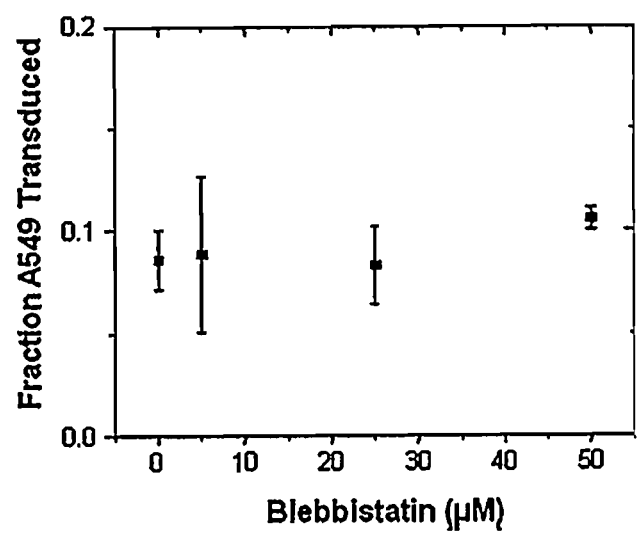

FIG. 20 illustrates that blebbistatin has no effect on lentivirus transduction in A549 cells. Blebbistatin treated A549 cells at various concentration was infected with lentivirus at an MOI of 270. Infection was quantified by RFP expression by fluorescent microscopy. (n≥3, ±SD).

DETAILED DESCRIPTION OF THE INVENTION

The present invention encompasses viral particles that include a surface marker, for example, CD47, for the purpose of disguising foreign particles thereby disabling macrophage engulfment of the viral particle. Thus, there is provided in the invention compositions and methods whereby viral particles that contain the therapeutic and diagnostic effects may evade phagocytosis and have a longer half life when administered to a mammal, preferably a human. Further, the viral particles contemplated herein provide a superior drug delivery system as compared with larger, micro-scale particle systems. The viral particles of the present invention have enhanced stability, enhanced carrier capacity, greater feasibility for incorporation of both hydrophilic and hydrophobic substances, and further have greater feasibility of variable routes of administration, including oral application and inhalation, as compared to previously known micro-scale particle drug carriers. The present invention also provides for controlled and/or sustained drug release from the viral particles, without losing the other benefits described above. These properties all suggest that the viral particles contemplated herein improve or enhance drug bioavailability and can reduce the dosing frequency, as compared to those micro-scale particle systems.

Definitions

As used herein, each of the following terms has the meaning associated with it in this section.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody" as used herein, refers to an immunoglobulin molecule, which is able to specifically bind to a specific epitope on an antigen. Antibodies may be intact immunoglobulins derived from natural sources or from recombinant sources and may be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies.

The term "biologically active" as used herein relative to CD47 or a portion thereof, means a full length or fragment of CD47, that when presented in a viral particle recognizes and binds to SIRPα in vivo in a human. The CD47 fragment may be any length fragment ranging from 10 to 304 amino acid length chains, and preferably between about 15 and 150 amino acid length chains, and any and all increments there between. A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, a disease or disorder is "alleviated" if the severity of a symptom of the disease or disorder, the frequency with which such a symptom is experienced by a patient, or both, are reduced.

As used herein, the term "immunoglobulin" or "Ig" is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "recombinant DNA" as used herein is defined as DNA produced by joining pieces of DNA from different sources.

As used herein, the term "polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides.

The term "peptide" typically refers to short polypeptides.

The term "conservative amino acid substitution" as used herein refers to replacement of an amino acid with a functionally and biochemically equivalent amino acid. These substitutions provide similar or enhanced function of a peptide. Functionally-equivalent amino acids are amino acids which share a common structure, side chain, polarity, and so forth. Examples of amino acids, by non-limiting example only, which may be functionally equivalent are:

| | |
|---|---|
| hydrophobic | Ala, His, Ile, Leu, Met, Phe, Trp, Tyr, Val |
| neutral hydrophilic | Cys, Ser, Thr |
| polar | Asn, Gln, Ser, Thr |
| acidic/negatively charged | Asp, Glu |
| charged | Arg, Asp, Glu, His, Lys |
| basic/positively charged | Arg, His, Lys |
| basic | Arg, Asn, Gln, His, Lys |
| residues that influence chain orientation | Gly, Pro |
| aromatic | His, Phe, Trp, Tyr |

Conventional notation is used herein to portray polypeptide sequences: the left-hand end of a polypeptide sequence is the amino-terminus; the right-hand end of a polypeptide sequence is the carboxyl-terminus.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are culture in vitro. In other embodiments, the cells are not cultured in vitro.

As used herein, a "therapeutically effective amount" is the amount of a therapeutic composition sufficient to provide a beneficial effect to a mammal to which the composition is administered.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "prophylactic treatment" as used herein is a treatment administered to a subject who does not exhibit signs of a disease or exhibits only early signs of the disease for the purpose of decreasing the risk of developing pathology associated with the disease.

The term "therapeutic treatment" as used herein is a treatment administered to a subject who exhibits signs of pathology for the purpose of diminishing or eliminating those signs.

The phrase "under transcriptional control" or "operatively linked" as used herein means that the promoter is in the correct location and orientation in relation to a polynucleotide to control the initiation of transcription by RNA polymerase and expression of the polynucleotide.

The term "virus" as used herein is defined as a particle consisting of nucleic acid (RNA or DNA) enclosed in a protein coat, with or without an outer lipid envelope, which is capable of replicating within a whole cell.

The term "CD47" means the protein encoded by the CD47 gene. The term "RBC" means red blood cell. The term "SIRPα" means signal regulatory protein alpha. The term "NMM IIA" means non-muscle myosin IIA. The term "nano" means any object that is less than about 1 μm in length. The term "micro" means any object that is between about 1 μm to 1000 μm in length Description The present invention includes viral particles designed to evade phagocytic uptake by immune cells. These viral particles may be used as drug carriers or drug delivery vehicles that improve drug bioavailability and reduce dosing frequencies. The viral particles of the invention also provide controlled or sustained drug release from either within the viral particle or internal vesicle or from the viral particle surface.

Viral Particles.

According to an aspect of the present invention, a viral particle is provided that is generally described as a submicron viral particle. As used herein, viral particle may also mean a virion. Preferably, the viral particle of the present invention has a radius of between about 50 nm and 1000 nm, and any and all whole or partial increments there between. More preferably, the viral particle has a radius of between about 100 nm to 400 nm, and any and all whole or partial increments there between.

In a preferred embodiment, a lentivirus is used to form the viral particle of the invention. Other viruses that are useful to generate the viral particle of the invention include any enveloped virus that naturally acquires its lipid envelop by budding through the cytoplasmic membrane. By non-limiting example, families such as poxyiridae and hepadnaviridae, as well as viruses such as retrovirus, adeno-associated virus, or chimera viruses with a simian immunodeficiency virus coated with the envelope proteins, G-protein, from vesicular stomatitis virus (VSV G-pseudotyped), are all contemplated by the present invention.

Expression of Surface Markers on Viral Particles.

According to an aspect of the present invention, the viral particle described herein may express a surface marker to improve agent or drug targeting, signaling, timed or sustained release, or other features effecting agent or drug bioavailability. Viral vector technology is well known in the art and is described, for example, in Sambrook et al., 2001, Molecular Cloning: A Laboratory Manual, Cold Spring Harbor Laboratory, New York, N.Y., and in other virology and molecular biology manuals. Viruses, which are useful as vectors include, but are not limited to, retroviruses, adenoviruses, adeno-associated viruses, herpes viruses, and lentiviruses, and any other viruses as described herein. In general, a suitable vector contains an origin of replication functional in at least one organism, a promoter sequence, convenient restriction endonuclease sites, and one or more selectable markers (See, e.g., WO 01/96584; WO 01/29058; and U.S. Pat. No. 6,326,193.).

For expression of the surface marker, at least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements, i.e., enhancers, regulate the frequency of transcriptional initiation. Typically, these are located in the region 30-110 by upstream of the start site, although a number of promoters have recently been shown to contain functional elements downstream of the start site as well. The spacing between promoter elements frequently is flexible, so that promoter function is preserved when elements are inverted or moved relative to one another. Depending on the promoter, it appears that individual elements can function either co-operatively or independently to activate transcription.

A promoter may be one naturally associated with a gene or polynucleotide sequence, as may be obtained by isolating the 5' non-coding sequences located upstream of the coding segment and/or exon. Such a promoter can be referred to as "endogenous." Similarly, an enhancer may be one naturally associated with a polynucleotide sequence, located either downstream or upstream of that sequence. Alternatively, certain advantages will be gained by positioning the coding polynucleotide segment under the control of a recombinant or heterologous promoter, which refers to a promoter that is not normally associated with a polynucleotide sequence in its natural environment. A recombinant or heterologous enhancer refers also to an enhancer not normally associated with a polynucleotide sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (U.S. Pat. Nos. 4,683,202 and 5,928,906). Furthermore, it is contemplated the control sequences that direct transcription and/or expression of sequences within non-nuclear organelles such as mitochondria, chloroplasts, and the like, can be employed as well.

It may be important to employ a promoter and/or enhancer that effectively directs the expression of the DNA segment in the cell type, organelle, and organism chosen for expression. Those of skill in the art of molecular biology generally know how to use promoters, enhancers, and cell type combinations for protein expression, for example, see Sambrook et al., 2001, Molecular Cloning: A Laboratory Manual" Cold Spring Harbor Laboratory, New York, N.Y. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous. In one embodiment, the promoter sequence may be the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, Moloney virus promoter, the avian leukemia virus promoter, Epstein-Barr virus immediate early promoter, Rous sarcoma virus promoter, as well as human gene promoters such as, but not limited to, the actin promoter, the myosin promoter, the hemoglobin promoter, and the muscle creatine promoter. Further, the invention should not be limited to the use of constitutive promoters. Inducible promoters are also contemplated as part of the invention. The use of an inducible promoter in the invention provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. Further, the invention includes the use of a tissue specific promoter, which promoter is active only in a desired tissue. Tissue specific promoters are well known in the art and include, but are not limited to, the HER-2 promoter and the PSA associated promoter sequences.

In the production of viral particles, a second vector encoding any required capsid, envelope and/or matrix proteins is introduced as a transient transfection of the cell line to provide for effective viral particle formation. During construction of the virion, the expressed surface marker may be incorporated into the virion along with the other viral proteins.

In order to assess the expression of the surface marker, the expression vector to be introduced into a cell can also contain either a selectable marker gene or a reporter gene or both to facilitate identification and selection of expressing viral particles from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. Expression of the reporter gene is assayed at a suitable time after the DNA has been introduced into the recipient cells.

Suitable reporter genes may include genes encoding luciferase, beta-galactosidase, chloramphenicol acetyl transferase, secreted alkaline phosphatase, or the green fluorescent protein gene (see, e.g., Ui-Tei et al., 2000, FEBS Lett. 479: 79-82). Suitable expression systems are well known and may be prepared using well known techniques or obtained commercially. Internal deletion constructs may be generated using unique internal restriction sites or by partial digestion of non-unique restriction sites. Constructs may then be transfected into cells that display high levels of the desired polynucleotide and/or polypeptide expression. In general, the construct with the minimal 5' flanking region showing the highest level of expression of reporter gene is identified as the promoter. Such promoter regions may be linked to a reporter gene and used to evaluate agents for the ability to modulate promoter-driven transcription.

In the context of an expression vector, the vector can be readily introduced into a host cell, e.g., mammalian, bacterial, yeast or insect cell by any method in the art. For example, the expression vector can be transferred into a host cell by physical, chemical or biological means. It is readily understood that the introduction of the expression vector comprising the polynucleotide of the invention yields a silenced cell with respect to a cytokine signaling regulator.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2001, Molecular Cloning: A Laboratory Manual, Cold Spring Harbor Laboratory, New York, and in Ausubel et al., 1997, Current Protocols in Molecular Biology, John Wiley & Sons, New York).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In a preferred embodiment, the viral particle includes a CD47 protein or peptide, or a portion thereof, expressed thereon. The CD47 protein may be the full-length protein, or it may a portion of the protein, wherein the portion is biologically active as defined herein. Preferably, the portion of CD47 includes at least a portion of the extracellular domain that interacts with SIRPα.

The full length amino acid sequence of human CD47 is:

```
                                           (SEQ ID NO: 1)
MWPLVAALLLGSACCGSAQLLFNKTKSVEFTFCNDTVVIPCFVTNMEAQ

NTTEVYVKWKFKGRDIYTFDGALNKSTVPTDFSSAKIEVSQLLKGDASL

KMDKSDAVSHTGNYTCEVTELTREGETIIELKYRVVSWFSPNENILIVI

FPIFAILLFWGQFGIKTLKYRSGGMDEKTIALLVAGLVITVIVIVGAIL

FVPGEYSLKNATGLGLIVTSTGILILLHYYVFSTAIGLTSFVIAILVIQ

VIAYILAVVGLSLCIAACIPMHGPLLISGLSILALAQLLGLVYMKFVAS

NQKTIQPPRNN.
```

The extracellular domain of human CD47 that interacts with SIRPα and is biologically active is:

```
                                           (SEQ ID NO: 2)
MWPLVAALLLGSACCGSAQLLFNKTKSVEFTFCNDTVVIPCFVTNMEA

QNTTEVYVKWKFKGRDIYTFDGALNKSTVPTDFSSAKIEVSQLLKGDA

SLKMDKSDAVSHTGNYTCEVTELTREGETIIELKYRVVSWFSPN
```

In the case of a partial protein or peptide fragment, a generic spacer domain may be fused to the amino acid chain of CD47, so that any required structural features of the partial protein or peptide fragment that contains biological activity are not disrupted. In other embodiments involving a partial protein or peptide fragment, a transmembrane domain or other membrane-anchoring functional domain may be fused to the biologically active CD47 protein fragment, such that the final recombinant protein effectively anchors into the viral particle envelope.

It will be appreciated by one skilled in the art that the invention should be construed to include CD47 proteins or peptides comprising conservative amino acid substitutions, provided that any such substituted CD47 molecules retains biological activity as that term is defined herein.

The surface marker, such as CD47, for example, may further be modified to include various tagging or labeling of any sort that provides for attachment of the surface marker to the viral particle. In one exemplary embodiment, the full length CD47 may be fused to the reporter green fluorescent protein.

The surface marker, e.g. CD47, may be expressed in the viral particle on the surface thereof, within the viral particle, or as a combination of both, provided that when the viral particle is administered to the subject, the exposed surface marker has the biological activity of evading phagocytosis by the phagocytic cell.

The surface marker included in the viral particle must be of a sufficient concentration so as to effectively signal, or be recognized by, other materials surrounding the viral particle. This concentration can be measured as a ratio of the number of surface marker (molecules) per $\mu m^2$. In one exemplary embodiment, the density (or concentration) of CD47 marker may approach that of surface markers found naturally in red blood cells (RBCs), which is approximately 250 molecules/$\mu m^2$. In other embodiments, the density of the CD47 marker may be as low as 20 molecules/$\mu m^2$, or it may be any amount between 20 and 250 molecules/$\mu m^2$, and any and all whole or partial increments there between. It should be appreciated that, provided such surface marker density is effective from a biological activity standpoint, that the density may be substantially lower or higher than the density of the CD47 as is found naturally on RBCs.

In a preferred embodiment, full-length human CD47 were amplified, digested and ligated to viral vector containing the green fluorescent protein gene, which resulted in an in-frame fusion of green fluorescent protein at the C terminus of full-length CD47 gene. For generation of overexpressed human CD47 viral particles, a dual transfection of vesicular stomatitis virus-G protein-pseudotyped viron (VSV-g) and the human CD47-GFP vectors were transiently transfected into human cells. This results in the viral envelope expressing the human CD47-GFP recombinant protein.

Methods of Using the Viral Particles of the Invention.

The present invention includes a method of evading uptake of viral particles by a phagocytic cell. The method comprises the steps of expressing at least one peptide comprising at least a biologically active portion of CD47 to envelope of the viral particle, and exposing the viral particle to an environment containing phagocytic cells, wherein the half life of the viral particle exposed in the environment is increased as compared to the viral particle that does not include a CD47 peptide.

In one embodiment, the present invention also includes a method of treating a subject for a medical condition identified as being in need of such treatment. The method comprises administering the aforementioned viral particles carrying an effective amount of a therapeutic compound, or a pharmaceutical composition comprising the therapeutic compound, as described herein, to an individual in need to such treatment. Medical conditions for treatment may include, by non-limiting example, cancer therapeutics and tumor detection, heart attack, blood clotting, diabetes, gene therapy, antisense therapy, artificial oxygen delivery, anti-inflammatory disease, Huntington's disease, Alzheimer's disease, arthritis, and muscular dystrophy. Other treatments contemplated may involve RNA interference or gene silencing, with the advantage of reducing or eliminating immune response from viral particle therapies. In another embodiment, the invention includes a method of prophylactic treatment of mammals comprising administrating the aforementioned viral particles carrying an effective amount of a therapeutic compound, or a pharmaceutical composition comprising the therapeutic compound, as described herein.

Compounds for delivery via the viral particles contemplated herein include therapeutic, prophylactic, and diagnostic agents. Any suitable agent may be used. These include organic compounds, inorganic compounds, hydrophobic or hydrophilic pharmacological drugs, radiopharmaceuticals, biologics, proteins, peptides, polysaccharides, nucleic acids, siRNA, RNAi or other materials that can be incorporated into the viral particles using standard techniques.

The amount of the therapeutic compound of the invention that will be effective in the treatment of a particular disorder or condition will depend on the nature of the disorder or condition, and is determined by the artisan skilled in the art. The precise dose to be employed, and the precise formulation used will depend on the route of administration and the severity of the disease, disorder, or condition, the age and gender of the subject and other parameters as determined by the skilled artisan Pharmaceutical Compositions One or more active agents may be formulated alone or with excipients or encapsulated on, in or incorporated into the viral particles of the present invention. Active agents may include therapeutic, prophylactic, and diagnostic agents. Any suitable agent may be used. These may include organic compounds, inorganic compounds, proteins, polysaccharides, nucleic acids or other materials that can be incorporated using standard techniques. Active agents include synthetic and natural proteins (including enzymes, peptide-hormones, receptors, growth factors, antibodies, signaling molecules), and synthetic and natural nucleic acids (including RNA, DNA, antisense RNA, triplex DNA, inhibitory RNA (RNAi), and oligonucleotides), and biologically active portions thereof. Suitable active agents have a size greater than about 1,000 Da for small peptides and polypeptides, more typically at least about 5,000 Da and often 10,000 Da or more for proteins. Nucleic acids with lengths above about 10 by are typically used in the present method. More typically, useful lengths of nucleic acids for probing or therapeutic use will be in the range from about 20 by (probes; inhibitory RNAs, etc.) to tens of thousands of by for genes and vectors. The active agents may also be hydrophilic molecules, preferably having a low molecular weight.

Compounds which are identified using any of the methods described herein may be formulated and administered to a mammal for treatment of the diseases disclosed herein are now described.

The invention encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs, birds including commercially relevant birds such as chickens, ducks, geese, and turkeys.

Pharmaceutical compositions that are useful in the methods of the invention may be prepared, packaged, or sold in formulations suitable for oral, rectal, vaginal, parenteral, topical, pulmonary, intranasal, buccal, ophthalmic, intrathecal or another route of administration. Other contemplated formulations include projected viral particles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient in an aqueous or oily liquid carrier. Such drops may further comprise buffering agents, salts, or one or more other of the additional ingredients described herein. Other ophthalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

Typically dosages of the compound of the invention which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 mg to about 10 g per kilogram of body weight of the animal. More preferably, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

Kits

The invention also includes a kit comprising the various compositions of the invention and an instructional material which describes adventitially administering the compositions to a cell or a tissue of a mammal. In another embodiment, this kit comprises a (preferably sterile) solvent suitable for dissolving or suspending the composition of the invention prior to administering the compound to the mammal.

As used herein, an "instructional material" includes a publication, a recording, a diagram, or any other medium of expression which can be used to communicate the usefulness of the compounds of the invention in the kit for effecting alleviation of various diseases or disorders. Optionally, or alternately, the instructional material may describe one or more methods of alleviation particular diseases or disorders in a cell or a tissue of a mammal. The instructional material of the kit of the invention may, for example, be affixed to a container which contains the compositions of the invention or be shipped together with a container which contains the compositions. Alternatively, the instructional material may be shipped separately from the container with the intention that the instructional material and the compounds be used cooperatively by the recipient.

Macrophage Recognition of CD47 is Species Specific

Figure 1:
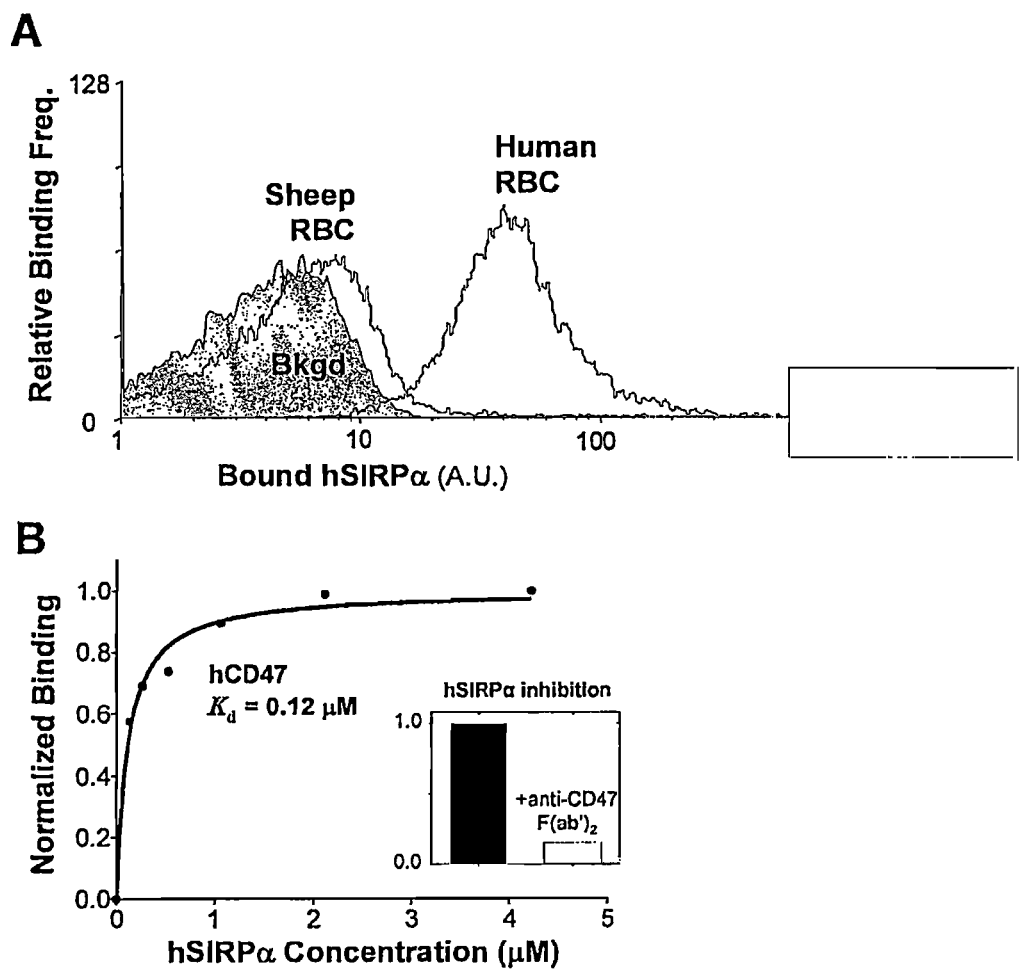

Human macrophages internalize particles through discrete signals initiated from extracellular communications with a target resulting in cytoskeletal remodeling (Kovacs, M., et al., (2003). J Biol Chem 278(40): 38132-40) and contractile forces (Allen, L. H. et al., (1995). J. Exp. Med. 182(3): 829-840; Swanson, J. A., et al., (1999). J Cell Sci 112(3): 307-316) leading to engulfment. These human macrophages are able to discern targets from non-self and self through the CD47 ubiquitous marker (Lindberg, F. P., et al., (1994). J Biol Chem 269(3): 1567-70). CD47 in mouse (Oldenborg, P. A., et al., (2000). Science. 288(5473): 2051-4; Gardai, S. J., et al. (2005). 123(2): 321) and humans (Tsai, R. K. et al., (2008). J Cell Biol 180(5): 989-1003) has been well-documented as a 'Marker of Self' that can inhibit phagocytosis by macrophages. Here, species of RBC from both humans and sheep were been used to characterize phagocytosis. As shown in FIG. 1A, soluble human-SIRPα was found to bind much less to sheep RBCs than to human RBCs. This result is consistent with previous reports showing species-specific CD47-SIRPα interactions (Subramanian, S., et al., (2006). Blood Cells, Molecules, and Diseases 36(3): 364-372).

To further eliminate potential differences between species, avidin-coated microbeads that display recombinant, biotinylated human CD47 were constructed. Plasmid encoding the extracellular domain of human CD47 were PCR amplified, digested with XbaI & SalI (New England Biolabs, Beverly, Mass.) and ligated to similarly digested vector, pEF-BOS-XB (Vernon-Wilson, E. F., et al., (2000). "Eur J. Immunol. 30(8): 2130-7), which resulted in an in-frame fusion of CD4d3+4-biotin at the c-terminus of the extracellular domain of CD47. The above vector containing the extracellular domain of CD47 was transfected into CHO (-K1) cells using Lipofectamine 2000 (Invitrogen). Secreted CD47-CD4d3+4 was concentrated using a 10K MWCO Amicon (Millipore) and biotinylated at the c-terminus using a biotin-protein ligase (Avidity, LLC) and dialyzed against PBS (Invitrogen). The protein was affinity-purified using a monomeric avidin (Promega, Madison, Wis.) and dialyzed against PBS (Invitrogen). To prepare and quantify CD47 density on polystyrene beads, streptavidin coated polystyrene beads of diameter 2.1 μm (Spherotech, Libertyville, Ill.) were washed and blocked 3× in PBS plus 0.4% BSA. The biotinylated human CD47 was attached to streptavidin coated beads at room temperature for 30 min and washed 3× and resuspended in PBS plus 0.4% BSA. The density of human CD47 present on the beads was labeled with saturating levels of B6H12-FITC and mIAP301-FITC (BD Biosciences) respectively for 30 min at room temperature. Beads were washed and resuspended in PBS/0.4% BSA and stored on ice until flow cytometric analysis. Mean fluorescence intensities were calibrated against uncoated streptavidin beads labeled with saturating B6H12-FITC/mIAP301-FITC levels. The fluorescent intensities were standardized using Quantum FITC Molecule of Equivalent Soluble Fluorochrome (MESF) units (Bangs Laboratories, Fishers, Ind.). The MESF value for the human CD47 beads was then divided by the number of fluorophore per antibody to obtain the number of molecules per bead. The density of CD47 molecules on the streptavidin bead was determined for the bead by dividing the surface area (SA) of the 2.1 μm bead (SA=13.9 μm$^2$). The density of CD47 molecules on human RBC (SA=128 μm$^2$) was also determined as described for the CD47 beads.

As shown in FIG. 1B, these beads demonstrate a moderate affinity and saturable interaction of CD47 for SIRPα and also establish effective blocking of CD47 (B6H12) with a F(ab')$_2$ made from a monoclonal antibody that is known to inhibit SIRP a binding. The dissociation constant, $K_d$ was given by the saturation binding fit. As this was a 3D binding constant relevant to binding in a narrow membrane gap between two cells, it was equivalent to $K_d$≈1 molecule/[10 nm×(10 mm)$^2$], which is the concentration of free SIRPα that would half-saturate CD47 on a surface. The inset shows the inhibition of soluble hSIRPα binding to hCD47-beads by using anti-CD47 F(ab)$_2$ generated from B6H12 antibody. Similar inhibition was obtained with human-RBC.

To assess the effect of CD47 on protein localization to the phagocytic synapse, human-derived THP-1 macrophages were incubated either with IgG-opsonized human RBCs or sheep RBCs. The RBCs were allowed to settle and bind macrophages at 4° C. 10 minutes after the RBCs were warmed to 37° C., cells were fixed and immunostained for imaging. As shown in FIG. 2A, imaging by differential interference contrast (DIC) microscopy provided an unbiased identification of phagocyte—RBC contacts. Subsequent immunofluorescence showed that human-RBCs in contact with human macrophages stimulated accumulation of SIRPα at the synapse. As shown in FIG. 1B, such localization was lacking both with sheep RBC and after blocking human RBC with F(ab')$_2$ of the anti-CD47. The removal of the Fc domain ensured no activating signal. As shown in the top panel of FIG. 2B, quantitative intensity analyses of randomly chosen synapses showed a fivefold enrichment of SIRPα with human—RBC contacts when compared with either sheep RBCs or CD47-blocked human RBCs.

Further, tyrosine phosphorylation is known to be strongly enhanced when macrophages phagocytose IgG-opsonized targets. Compared with SIRPα, phosphotyrosine showed the opposite trends after immunostaining. As shown in the lower panel of FIG. 2B, synapses with human RBCs showed only a small increase of phosphotyrosine above cytoplasmic levels and at a level that was 3.2-fold lower than sheep RBCs or CD47-blocked human RBCs. IgG interactions with Fc receptors (FcγRs) are also known to initiate Src family phosphorylation of the immunoreceptor tyrosine-based activating motif (ITAM) that then propagate a phosphorylation cascade (Huang, M. M., et al., (1992). J Biol Chem 267(8): 5467-73; Ghazizadeh, S., et al. (1994). J Biol Chem 269(12): 8878-84; Greenberg, S., et al., (1994). J. Biol. Chem. 269(5): 3897-3902). In contacts with human RBCs, however, the CD47-induced accumulation of SIRPα at the synapse phospho-activates the immunoreceptor tyrosine-based inhibiting motif (ITIM) of SIRPα (Kharitonenkov, A., Z. et al., (1997). Nature 386(6621): 181-6) with subsequent recruitment of inhibitory tyrosine phosphatases, particularly SHP-1 (Tsuda, M., et al., (1998). J Biol Chem 273(21): 13223-9; Veillette, A. et al., (1998). J Biol Chem 273(35): 22719-28; Vernon-Wilson, E. F., et al., (2000)." Eur J. Immunol. 30(8): 2130-7; Kant, A. M. et al., (2002). Blood 100(5): 1852-1859). This phosphatase activation is consistent with the relatively large and dominant decrease found for phosphotyrosine.

Pseudopod extension and phagocytic cup formation around a target requires extensive remodeling of the actin cytoskeleton. It has also previously been suggested that non-muscle myosin may play a role in phagocytosis (Mansfield, P. J. et al., (2000). Blood 95(7): 2407-2412). Surprisingly, as shown in FIGS. 2C and the top panel of FIG. 2D, SIRPα-CD47 interactions did not exert any statistically significant effect (P=0.3) on F-actin localization to the synapse. However, as shown in FIGS. 2C and the bottom panel of FIG. 2D, immunofluorescence for the dominant myosin isoform, nonmuscle myosin IIA (NMM IIA), shows clear recruitment to both sheep RBCs and CD47-blocked human RBCs. Localization of myosin to the synapse with human RBCs appears to be minimal, with a 3.8-fold decrease relative to sheep RBCs and CD47-blocked human RBCs.

Figure 3:
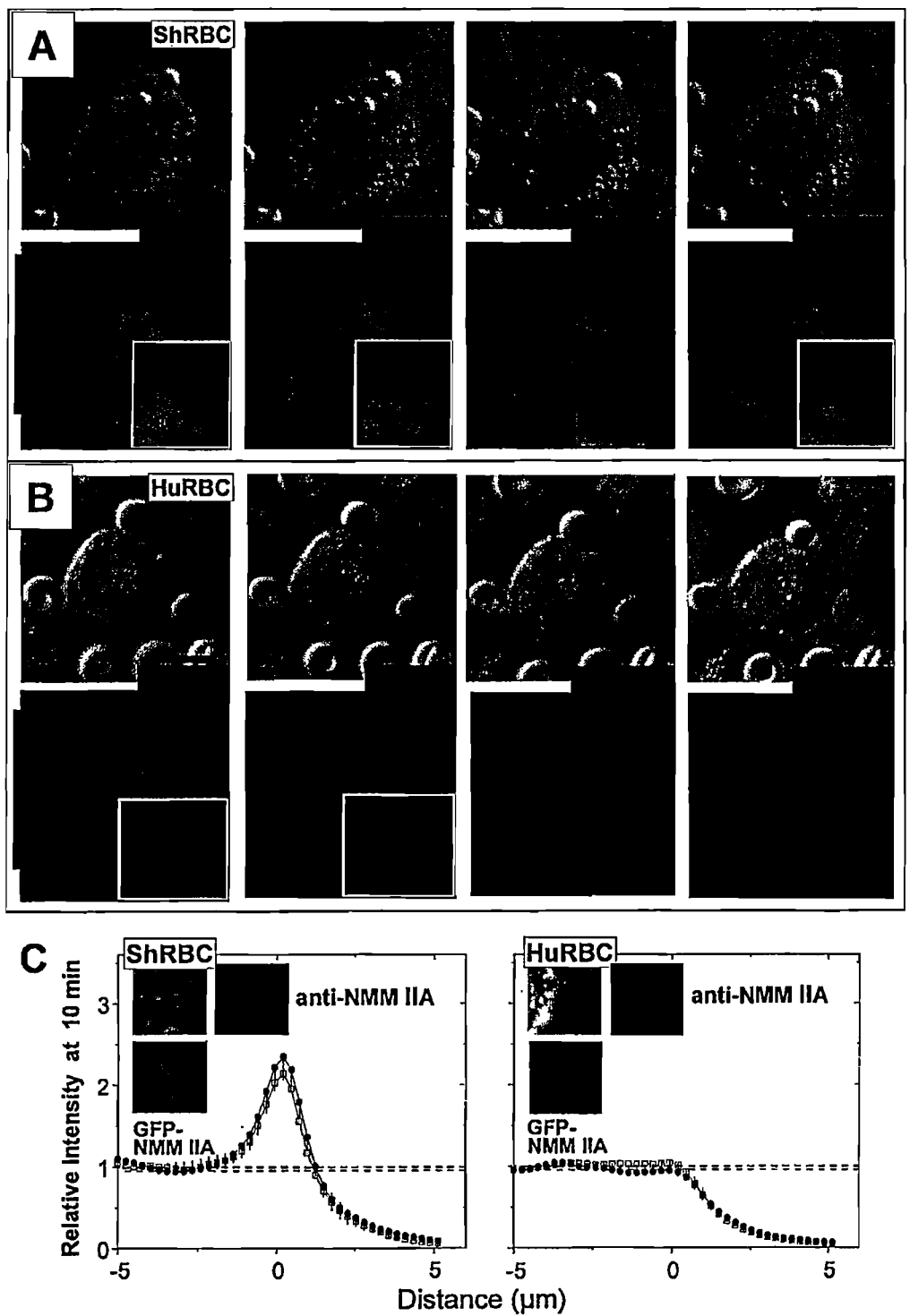

As shown in FIG. 3A, recruitment of NMM IIA to the synapse formed with sheep RBCs was seen to take only minutes and to persist typically for at least 15 minutes. Macrophages were stably transfected with GFP-NMM IIA, and real-time fluorescence imaging was used to follow the contact and engulfment process. As shown in FIGS. 3B and 3C, both sheep RBCs and human RBCs adhered and engaged the macrophages, initiating the formation of a phagocytic cup. However, NMM IIA did not enrich adjacent to the human RBCs. RBC contacts per macrophage additionally showed no major difference in adhesion frequency (not shown), which is consistent with divergent events subsequent to adhesion.

Inhibition of Myosin Recruitment to the Phagocytic Synapse

Figure 4:
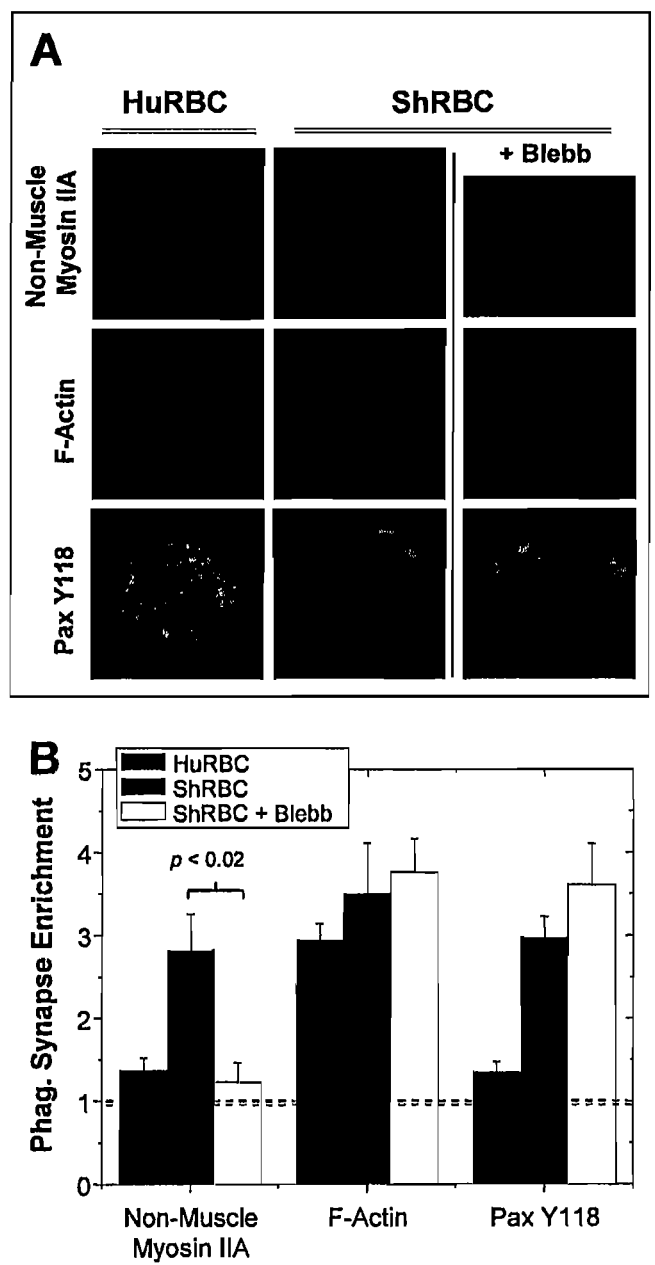

Nonmuscle myosin has long been known to be expressed in macrophages (Stendahl et al., 1980, J. Cell Biol. 84(2):215-24), and although reports have implicated myosin in FcγR-mediated phagocytosis (Swanson et al., 1999., J. Cell Sci. 112(3):307-316; Titus, 1999, Current Biology 9:1297-1303; Mansfield et al., 2000, Blood 95(7):2407-2412; Diakonova et al., 2002, Mol. Biol. Cell 13(2):402-11) through inhibition with 2,3-butanedione monoxime (BDM), this is a relatively nonspecific drug compared with blebbistatin (Ostap, 2002, J. Muscle Res. Cell Motil. 23:305-8; Limouze et al., 2004, J. Muscle Res. Cell Motil. 25:337-41). Blebbistatin is a membrane-permeable drug that inhibits ATPase activity of myosin types II and VI (Straight et al., 2003, Science 299(5613): 1743-7; Kovacs et al., 2004, J. Biol. Chem. 279(34):35557-35563). As shown in FIGS. 4A and 4B, incubation of macrophages with blebbistatin inhibited enrichment of NMM IIA at synaptic contacts with sheep RBCs targets. CD47 on human RBCs induced quantitatively similar effects on NMM IIA. In contrast, F-actin localization to the synapse again appeared statistically the same for sheep RBCs in the presence or absence of the myosin inhibitor as well as for CD47-blocked human RBCs.

Paxillin is also known from past studies to accumulate at the phagocytic synapse (Greenberg et al., 1994, J. Biol. Chem. 269(5):3897-3902) and to be phosphorylated (Hall, 1998, Science 279:509-14.). Also shown in FIG. 4A, phospho-paxillin $Y^{118}$ localized to the synapse with sheep RBCs and persisted with myosin inhibition by blebbistatin. In contrast, human RBCs inhibited phospho-paxillin localization through the effects of CD47. The double-labeling seen in FIG. 4A consistently shows statistically similar levels of F-actin localization, whereas phospho-paxillin varies. Phosphatase activity initiated by CD47-SIRPα interaction likely has multiple downstream targets that directly or indirectly include phospho-paxillin, as well as a novel phosphorylation site in myosin, as described hereinbelow.

Blocking Cd47 on Human Red Blood Cells (RBCs) Increases Phagocytosis

While previous reports on mouse cells has suggested that CD47 inhibits phagocytosis, there has been no evidence to date illustrating human phagocytes interacting with any type of target cell or particle. Referring again to FIG. 2, CD47-blocking of human RBCs with the F(ab')$_2$ was shown above to perturb the phagocytic synapse, which made the synapse look like that of sheep RBCs interacting with macrophages. Human CD47's interaction with SIRPα was blocked and engulfed by human phagocytes at a greater frequency than untreated, unblocked cells.

Figure 5:
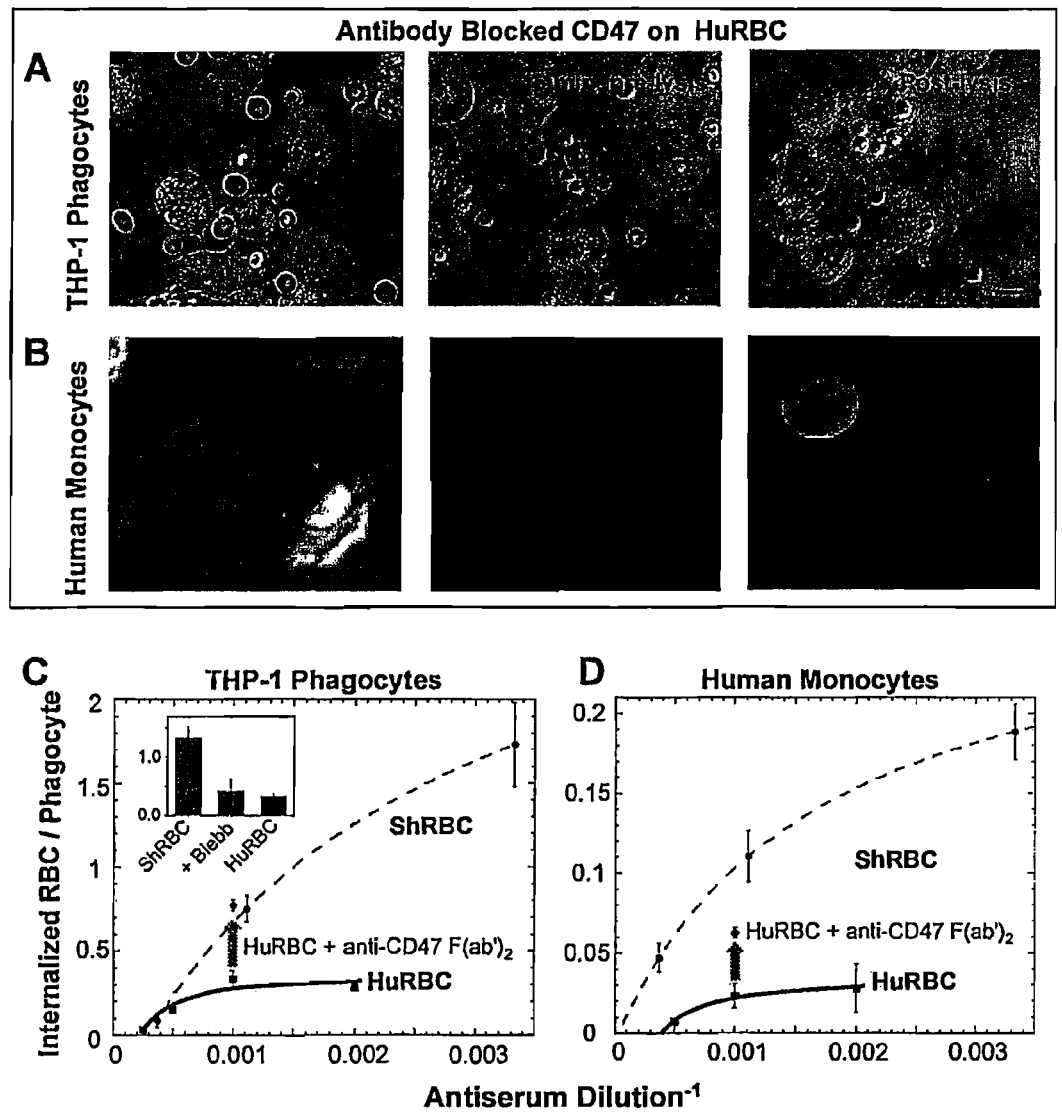

Phagocytosis by the human-derived THP-1 macrophages of IgG-opsonized RBCs was studied by imaging in DIC microscopy. As shown in FIG. 5A, after 45 minutes at 37° C., the non-engulfed RBCs were hypotonically lysed and the number of ingested RBCs per macrophage was counted. As shown in FIG. 5B, phagocytosis of RBCs by fresh human peripheral blood monocytes was visualized by using fluorescence. RBC membranes were prelabeled with PKH26, and non-engulfed RBCs were labeled with a fluorescein-labeled antibody against the Fc of the IgG-opsonin. As shown in FIGS. 5C and 5D, for either type of human phagocyte, human RBCs were internalized at a small fraction of the frequency of internalized sheep RBCs. A small number of human RBCs was engulfed for either type of phagocyte. Dependencies on IgG-opsonization fit well to a saturation binding process, which was consistent with specific activation of the FcR phagocytosis pathway. Based on these results, the blocking of CD47 on human RBCs produced significant increases in phagocytosis with two- to threefold more engulfment that approached or slightly exceeded the phagocytosis of sheep RBCs.

Nonmuscle Myosin IIA Contributes To Fcγr-Mediated Phagocytosis

In light of the myosin differences seen by fluorescence at the various synapses (FIGS. 2-4), the effect of blebbistatin-inhibited myosin on phagocytosis was studied. As shown in FIG. 5C, engulfment of sheep RBCs by THP-1 macrophages was found to be inhibited by blebbistatin to an extent similar to that of CD47 on human RBCs. Moreover, a dose–response gave a $K_{i-blebb}$=5 µM for blebbistatin inhibition of phagocytosis (not shown), which is consistent with the $K_{i-ATPase}$ for inhibition of NMM IIA's ATPase by blebbistatin (Limouze et al., 2004, J. Muscle Res. Cell Motil. 25:337-41).

To directly confirm the implied correlation between synaptic myosin and the extent of phagocytosis, fluorescence imaging was repeated on the enrichment of myosin and F-actin at the synapse for both human and sheep RBCs treated with or without blebbistatin. As demonstrated in FIGS. 4 and 5, when synaptic NMM IIA is at or near background cytoplasmic levels, phagocytosis is low but nonzero. The comparatively rapid enrichment of F-actin at the phagocytic synapse appears to be dependent primarily on the initial synaptic contact rather than the ultimate level of phagocytosis. This highlights a basal level of pseudopod extension and engulfment that is independent of myosin.

CD47 on Micro-Sized Beads Inhibits Phagocytosis

The extracellular immunoglobulin-like domains of human CD47 (hCD47) was recombinantly expressed with a spacer domain (Brown et al., 1994, Protein Eng. 7:515-21; Brown et al., 1998, J. Exp. Med. 188:2083-90) plus a C-terminal biotinylation site. As shown in FIG. 6A, biotinylation allowed attachment of soluble hCD47 to streptavidin-coated beads of approximately 2.1 µm in size, with a density adjustable to levels previously measured for normal and diseased RBCs (Dahl et al., 2004, Blood 103:1131-6; Subramanian, et al., 2006, Blood Cells Mol. & Dis. 36:364-372). The beads were opsonized by pretreatment with anti-streptavidin to again induce FcR-mediated phagocytosis (for 45 minutes at 37° C.), and non-engulfed beads were detected with a flourescein anti-Fc against the IgG-opsonin. The number of adherent IgG-opsonized beads per phagocyte was independent of hCD47 (not shown). Referring again to FIG. 5B, phagocytosed beads were sterically protected so that the merged DIC and fluorescent images provided a definitive means to quantify the internalized beads per phagocyte.

The phagocytosis results for beads were wholly consistent with the RBC results. As shown in FIG. 6B, with increasing opsonization and for both THP-1 cells and the human monocytes, the uncoated "CD47-null" beads were phagocytosed more than beads displaying hCD47. The dependence on the level of IgG-opsonization fit well to a saturation binding process, consistent again with the specificity of FcR-activated phagocytosis (See also FIGS. 5C and 5D). Likewise, blebbistatin inhibited phagocytosis of CD47-null beads to a level similar as hCD47 beads and again yielded a $K_{i\text{-}blebb}$ consistent with inhibition of NMM IIA's ATPase (not shown). This again confirmed the role of nonmuscle myosin. Furthermore, blocking CD47 on hCD47 beads produced an increase in phagocytosis, demonstrating that the Ig domain of human CD47 is sufficient to inhibit phagocytosis. As shown in FIG. 6C, inhibition of phagocytosis depends on density of human-CD47 on beads. Phagocytosis inhibition occurs with an effective $K_i \approx 20$ molecules/$\mu m^2$, which considerably exceeds the relevant dissociation constant for a 10 nm gap of $K_{d,10\ nm} \approx 1$ molecule/(10 $\mu m)^2$, as shown in FIG. 1B. This ratio of ~1000 as well as the known cell-surface densities imply that almost all SIRPα and CD47 that diffuse into the gap will bind and thus enrich in the synapse (See FIGS. 2A and 2B). A bar graph comparing hCD47 inhibition of phagocytosis in peripheral blood monocytes can be seen in FIG. 6D.

Density Dependence of CD47 in Species-Specific Inhibition of Phagocytosis

While studies of knockout mice have implicated CD47 as a marker of self on mouse RBCs (Oldenborg et al., 2000, Science 288(5473):2051-4); humans with major co-deficiencies of CD47 on their RBCs show no evidence of enhanced phagocytic interactions (Mouro-Chanteloup et al., 2003, Blood 101(1):338-344; Arndt et al., 2004, Br. J. Haematol. 125(3):412-4). Known and unknown differences between RBCs from different species also motivate a common phagocytic target. The hCD47-coated microbeads (FIG. 1) were thus used to establish the inhibitory density dependence of hCD47 with a common IgG-opsonin. These two ligands, hCD47 and IgG, do not compete and do not interfere with SIRPα binding (not shown).

As shown in FIGS. 6B and 6C, beads were opsonized at saturating densities of IgG, and over a 20-fold range of CD47 densities, the number of internalized beads per THP-1 was measured. Human CD47 gave a $K_i$ at high opsonin of 20 CD47/$\mu m^2$, which appears ~10-fold less than normal human RBC densities of CD47. As shown in FIG. 6D, human peripheral blood monocytes interacting with beads bearing high densities of hCD47 showed a similarly potent reduction in phagocytosis. A higher baseline level of bead phagocytosis versus RBCs could redirect the fact that stiffer targets are more readily engulfed (Beningo et al., 2002, J. Cell Sci. 115:849-856). More importantly, these results show that even 10-20% of normal CD47 densities are sufficient to inhibit phagocytosis.

Phagocytosis is Proportional to Myosin in the Absence of CD47

Figure 7:
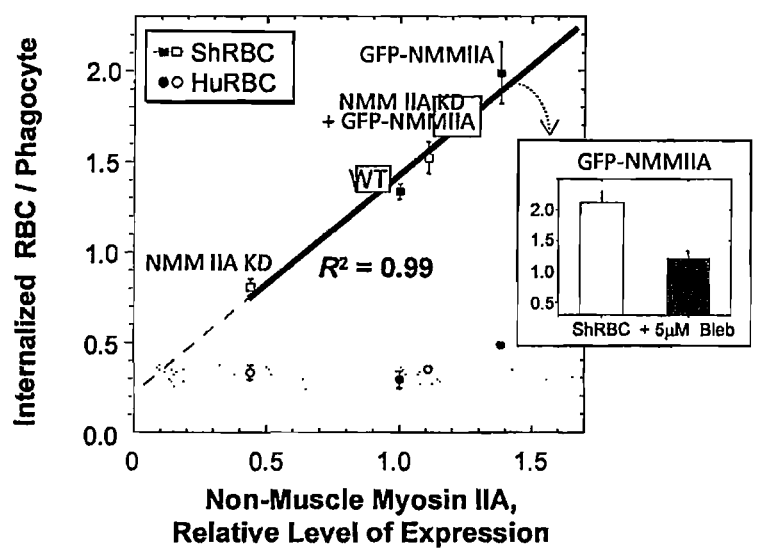

Inhibition of phagocytosis by blebbistatin functionally implicated NMM II because it inhibits all three isoforms (A-C). To more directly assess the function of the IIA isoform, the effects of both knockdown and overexpression were functionally studied. Transfection of GFP-NMM IIA added 50% more total IIA isoform, based on an immunoblot comparison to wild type (not shown). As shown in FIG. 7, this overexpression resulted in ~50% more phagocytosis of sheep RBCs. Similarly, knockdown of NMM IIA with Lentivirus gave ~50% less myosin, and this resulted in nearly 50% less phagocytosis. Transfection of GFP-NMM IIA into the knockdown cells, when driven by a CMV promoter, returned expression to near wild-type levels, and also recovered full phagocytic function. Also shown in FIG. 7, the GFP-NMM IIA was inhibited ~50% by 5 μM blebbistatin (inset), which again indicates that this chimeric construct has normal, myosin-like activity. A linear fit ($R^2=0.99$) through all of these phagocytosis results for sheep RBCs not only emphasizes the proportional role for myosin in efficient engulfment, but also yields a nonzero intercept at "zero" myosin activity that is nearly the same as the low rate for "actin only" engulfment of human RBCs (~0.2-0.3 RBC per macrophage). These results show that human CD47 parses pathways and primarily signals inhibition of NMM IIA's contribution to efficient phagocytosis.

CD47 Signals Through Sirpα and Ultimately to Myosin

SIRPα localization to the phagocytic synapse with targets presenting CD47 is consistent with ligand-receptor interactions as well as SIRPα ITIM activation and subsequent SHP-1 phosphatase induction (Brown et al., 2001, Trends Cell Biol. 11:130-5; Latour et al., 2001, J. Immunol. 167:2547-54). As shown in FIG. 8A, immunoprecipitation of SIRPα followed by Western blot analysis of phosphotyrosine showed a clear and saturable signaling difference with hCD47. The term denoted as $K_i$ is defined as the normalization of CD47 densities to the phagocytosis inhibition constant for human CD47 (FIG. 6C) and normalization of phosphotyrosine levels to SIRPα intensities gave an effective signaling constant $K_s$ that approximated the $K_i$ While CD47's activation of SIRPα (of about twofold) and downstream phosphatase activity has been reported, downstream phospho-targets have not yet been identified. Studies of SIRPα-knockout macrophages engulfing IgG-opsonized mouse RBCs (Okazawa et al., 2005, J Immunol 174(4):2004-11) suggested no major perturbation of either phospho-FcγR, downstream phospho-Syk or phospho-Cbl, although it had been reported that SHP-1 can dephosphorylate Cbl and thereby moderate Rac activity in FcγR-mediated phagocytosis (Kant et al., 2002, Blood 100(5):1852-1859). As shown in FIG. 8B, changes in the phosphorylation state of these activator/effector proteins ranged from 1.1-(FcγR) to 1.5-fold (Cbl). Considerably larger down-regulation of phosphotyrosine by CD47 at the synapse (3.2-fold) was clear in the imaging studies of FIG. 2B, as was CD47-induced delocalization of myosin and phospho-paxillin (3.8- and 3.0-fold, respectively; FIGS. 2D and 4B).

The only report of phosphotyrosine regulation of NMM IIA suggested it to be a direct target of SHP-1 in B-cells (Baba et al., 2003, Biochem. Biophys. Res. Comm. 304:67-72), with the speculated site of interaction appearing in the N-terminal head domain. Phosphotyrosine regulation of NMM IIA was therefore pursued in the context of CD47 function. As shown in FIG. 8C, anti-phosphotyrosine immunoblots were made from whole cell lysates of THP-1 cells phagocytosing opsonized human or sheep RBCs. Three band regions (a, b, c) showed the greatest differences in phosphotyrosine levels as compared with THP-1 cells alone. As shown in the plot of FIG. 8C, bands a-c each showed 3.3- to 1.6-fold less phosphotyrosine with human RBCs versus sheep RBCs, which was similar in range to the down-regulation of phosphotyrosine imaged at the phagocytic synapse (3.2-fold in FIG. 2B). In fact, band "a" had a MW in the range of nonmuscle myosins in addition to a similarly high level of down-regulation.

Phosphotyrosine bands a-c, were excised from Coomassie-stained polyacrylamide gels, digested in-gel by trypsin, and the peptide fragments were characterized by liquid chromatography-mass spectrometry/mass spectrometry (LC-MS/MS) (FIG. 8C, bottom). Within band "a", 45 tryptic peptides matched sequences of NMM IIA (23% coverage), including one fragment from myosin's self-assembling tail region with a novel phosphorylation at $Y^{1805}$. Additional cytoskeletal proteins that were detected in the macrophages and might be targeted in the CD47~SIRP phosphotyrosine pathway include Talin-1 (Turner et al., 1989, J. Biol. Chem. 264: 11938-44; Greenberg et al., 1990, J. Exp. Med. 172(6):1853-6), mDIA1 (Meng et al., 2004, EMBO J. 23:760-71), and ~-actinin (Crowley et al., 1995, J. Cell Biol. 131:525-37; Izaguirre et al., 1999, J. Biol. Chem. 274:37012-20). Capabilities of MS to identify phosphotyrosine are currently limited, as here, by low sequence coverage and sub-stoichiometric phosphorylation (McLachlin et al., 2001, Curr. Opin. Chem. Biol. 5:591-602). However, the one solid lead from MS of the phosphotyrosine in NMM IIA was first followed up by immunoprecipitation of NMM IIA from the THP-1 lysates and subsequent immunoblotting for phosphotyrosine, as shown in FIG. 8D. These results confirmed the presence of phosphotyrosine in NMM IIA that is ultimately regulated by CD47 interactions.

Phosphotyrosine Activation of NMM IIA in Phagocytosis

In light of the proportionality between phagocytosis and myosin expression (FIG. 7), several mutants of the GFP-NMM IIA construct were made and studied in their effects on phagocytosis of sheep RBCs and localization to the synapse. One mutant truncated the C terminus by 170 residues and had been found previously to compromise myosin ~lament assembly and function (Wei et al., 2000, Mol. Biol. Cell. 11:3617-27). Two Y→F point mutations were made at the putative phospho-sites in the head ($Y^{277}$) and tail ($Y^{1805}$). As shown in FIG. 9A, although the wild-type GFP-NMM IIA construct showed gain-of-function phagocytosis that was statistically distinct from untransfected wild type (P<0.03), all three mutants appeared the same as wild type. Similar results with even greater statistical significance (P<0.01) were found upon transfection of these constructs into the knockdown macrophages.

Consistent with the lack of a functional contribution to phagocytosis, as shown in FIG. 9B, the GFP mutants exhibited no significant localization to the synapse. The transfections of these GFP constructs into wild-type macrophages also allowed immunostaining for total NMM IIA. Quantitative ratio imaging (FIG. 2) showed that the endogenous myosin accumulated at phagocytic synapses, whereas the mutant constructs did not. These results contrast with the clear localization of the wild-type GFP-NMM IIA to the phagocytic synapse (FIG. 3A) and point to the role for phospho-regulation of myosin-II in phagocytosis.

Figure 2:
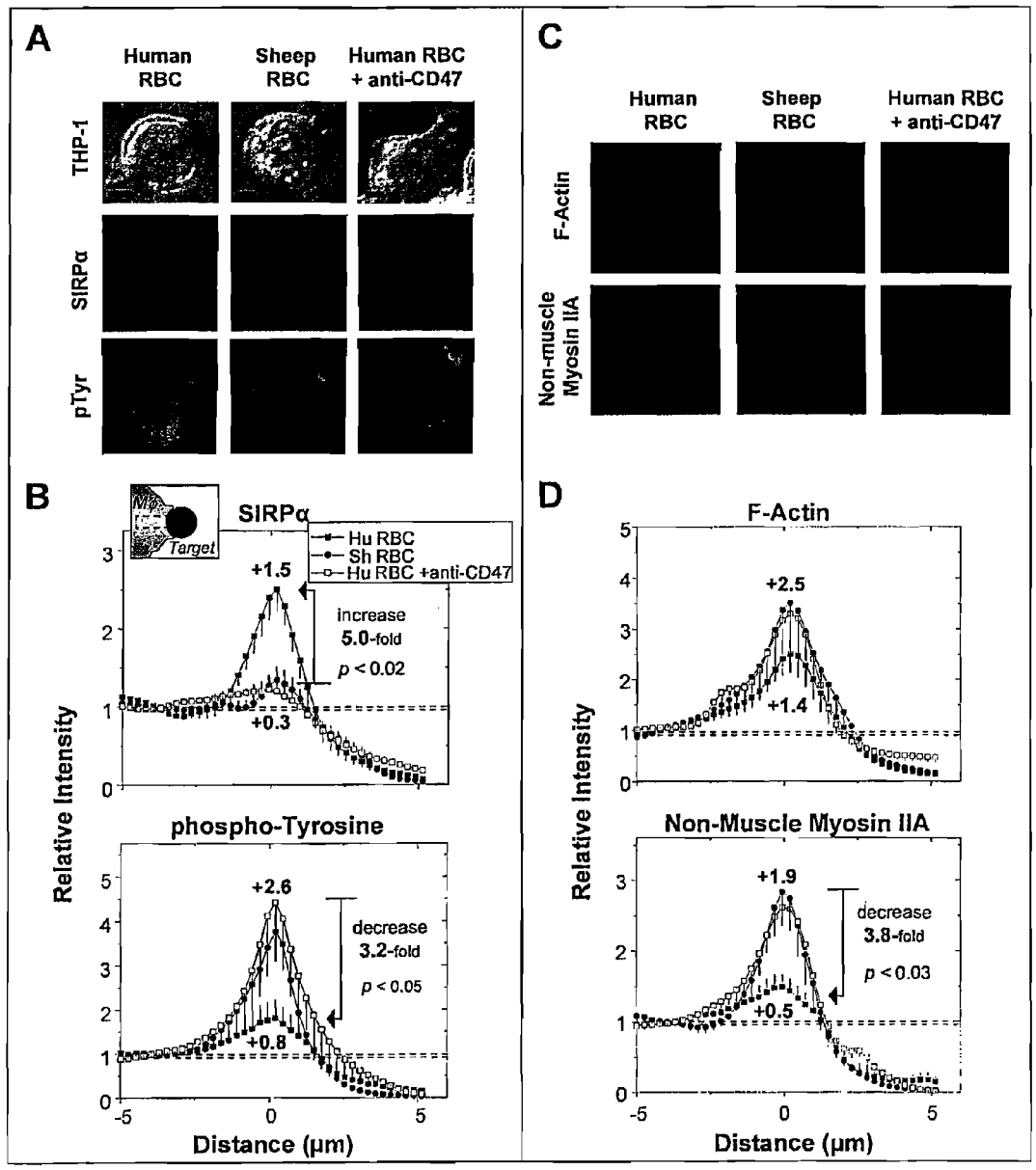

As shown in FIG. 10, the signaling and remodeling processes are highlighted. IgG activation of the Fc ~receptor on the phagocytes (Cambier, 1995, J. Immunol. 155:3281-5) is understood to induce actin cytoskeleton assembly (Araki et al., 1996, J. Cell Biol. 135:1249-60; Crowley et al., 1997, J. Exp. Med. 186:1027-39; Caron et al., 1998, Science 282: 1717-21; Lowry et al., 1998, J. Exp. Med. 187(2):161-76; May et al., 2001, J. Cell Sci. 114(Pt 6):1061-77), and this F-actin assembly is shown to be independent of CD47's signaling pathway(s) (FIG. 2). In the absence of CD47 on the target, paxillin assembles at the phagocytic synapse, consistent with past results for IgG-opsonized sheep RBCs (Greenberg et al., 1994, J. Biol. Chem. 269(5):3897-3902; Coppolino et al., 2001, J. Cell Sci. 114:4307-18), and so does NMM IIA. By contrast, human RBCs with functional CD47 show strong localization of the counter-receptor SIRPα to the synapse (fivefold), and also show strongly reduced levels of both phosphotyrosine and NMM IIA (3.2- and 3.8-fold, respectively; FIG. 2). Although CD47 signals locally, it ultimately has a similar, but downstream effect in inhibiting the major myosin isoform's contractile contributions to engulfment.

Given the low densities of CD47 on cells, this ubiquitous membrane protein seems less likely to mediate cell adhesion than function as an extremely potent signaling receptor, functional at densities of a just a few dozen molecules per $\mu m^2$ (FIG. 6C). Major co-deficiencies of CD47 on human cells (Mouro-Chanteloup et al., 2003, Blood 101:338-344) can therefore be tolerated without compromising the "marker of self" function.

Cytoskeletal Proteins Recruited to the Phagocytic Synapse of Nano-Scale Particles Consistent with recent results showing that self signal through CD47-SIRPα interaction is important in passivating phagocytosis of ≥1 μM particles and red blood cells (RBC) (FIG. 11A). It is desired to extend the implication of the CD47-SIRPα signaling observed in eukaryotic cells to nanoscale particles. However, potential differences between nano- and micro-sized targets exist. To specifically understand the contribution of CD47 as a self marker in targets at nanometer length scales, streptavidin-coated particles from 100 nm to 3.5 μm in size were attached with recombinant, biotinylated human CD47 (hCD47) (Tsai 2008) were used to explore the limits of self signal.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Chemicals:

DPBS without $Ca^{2+}$ or $Mg^{2+}$ (Invitrogen, Carlsbad, Calif.) was supplemented with either 1% BSA or 1% BSA and 0.05% Tween 20 (Sigma-Aldrich, St. Louis, Mo.). TBS (Tris Buffered Saline) and TTBS (TBS with Tween 20) were used in western blotting. Hoechst (Invitrogen, Carlsbad, Calif.) was used for DNA stains.

Antibodies:

Antibodies against human CD47 included B6H12-FITC (BD Biosciences). Human SIRPα$^{ex}$ for experiments comparing binding affinities between species was used. Antibodies against streptavidin coated polystyrene beads (Spherotech) included rabbit anti-streptavidin (Sigma-Aldrich) and rabbit anti-streptavidin conjugated with FITC (Rockland Immunochemicals) was used as IgG opsonin in phagocytosis assays. Secondary antibodies used for detecting opsonin levels and uningested beads included goat anti-rabbit FITC or goat anti-rabbit F(ab')$_2$ R-PE (Sigma-Aldrich). Secondary antibodies used for detecting SIRPα$^{ex}$ binding included anti-GST Alexa 488 (Invitrogen).

Cells and Cell Lines:

COS-1, CHO-K1, A549, and THP-1 cells (ATCC, Manassas, Va.) were respectively maintained in DMEM, MEMα, F-12 and RPMI 1640 media (Invitrogen) supplemented with 10% FBS (Sigma-Aldrich). Differentiation of THP-1 cells was achieved in 100 ng/mL phorbol myristate acetate (PMA) for 2 days and confirmed by attachment of these cells to tissue-culture plastic.

Soluble Human SIRPα Production:

COS-1 cells were transfected with pcDNA3-based vector (Seiffert, M., et al., (1999). Blood 94(11): 3633-43) encoding a human SIRPα extracellular domain fused to GST using Lipofectamine 2000 (Invitrogen). Secreted SIRPα1-GST (referred as hSIRPα$^{ex}$) was affinity-purified using Glutathione Sepharose 4B (Amersham Biosciences, Piscataway, N.J.) and dialyzed against PBS (Invitrogen). The protein was stored at −20° C. with or without addition of 10% v/v glycerol (Fisher Scientific, Hampton, N.J.).

Lentiviral Vector Construct:

The CS-CG HIV-1 transfer plasmid, modified as previously described, was used to generate a self-inactivating lentiviral vector (Naldini et al., 1996, Science 272(5259):263-7). Human CD47 were PCR-amplified, digested with XhoI and BamHI (New England Biolabs, Beverly, Mass.), and ligated to similarly digested vector, pEGFP-N3 (Clontech), which results in an in-frame fusion of EGFP at the C terminus of full-length CD47. Vesicular stomatitis virus-G protein-pseudotyped (VSV-g) with a CMV-Flag-MST (RFP) for control lentivirus particles were transiently transfected into human 293T cell lines and titered as previously described (Sena-Esteves et al., 2004, J. Virol. Methods 122(2):131-9). For generation of overexpressed human CD47 lentivirus, a dual transfection of VSV-g CMV-Flag-MST (RFP) and hCD47(FL)-GFP was transfected in the same cells as control resulting with envelope expressing the huCD47-GFP.

Production of Recombinant Human CD47:

Plasmid encoding the extracellular domain of human CD47, mouse CD47 were PCR amplified, digested with XbaI & SaII (New England Biolabs, Beverly, Mass.) and ligated to similarly digested vector, pEF-BOS-XB (Vernon-Wilson et al., 2000, Eur. J. Immunol. 30(8):2130-7), which results in an in-frame fusion of CD4d3+4-biotin at the c-terminus of the extracellular domain of CD47. The above vector containing the extracellular domain of CD47 was transfected into CHO (−K1) cells using Lipofectamine 2000 (Invitrogen). Secreted CD47-CD4d3+4 was concentrated using a 10K MWCO Amicon (Millipore) and biotinylated at the c-terminus using a biotin-protein ligase (Avidity, LLC) and dialyzed against PBS (Invitrogen). The protein was affinity-purified using a monomeric avidin (Promega, Madison, Wis.) and dialyzed against PBS (Invitrogen).

Preparation and Quantification of CD47 Density on Polystyrene Beads:

Streptavidin coated polystyrene beads of radius 100 nm (Ademtech), 160 nm, 1.1 μm, and 3.5 μm (Spherotech, Libertyville, Ill.) were washed and blocked 3× in PBS plus 0.4% BSA. Biotinylated human CD47 was attached to streptavidin coated beads at room temperature for 30 min and washed 3× and resuspended in PBS plus 0.4% BSA.

The density of human CD47 present on the beads was labeled with saturating levels of B6H12-FITC (BD Biosciences) for 30 min at room temperature. Beads were washed and resuspended in PBS/0.4% BSA and stored on ice until flow cytometric analysis. Mean fluorescence intensities were calibrated against uncoated streptavidin beads labeled with saturating B6H12-FITC. The fluorescent intensities were standardized using Quantum FITC Molecule of Equivalent Soluble Fluorochrome (MESF) units (Bangs Laboratories, Fishers, Ind.). The MESF value for the human CD47 beads was then divided by the number of fluorophore per antibody to obtain the number of molecules per bead. The density of CD47 molecules on the streptavidin bead was determined for the bead by dividing the surface area (SA) of each bead.

Figure 6:
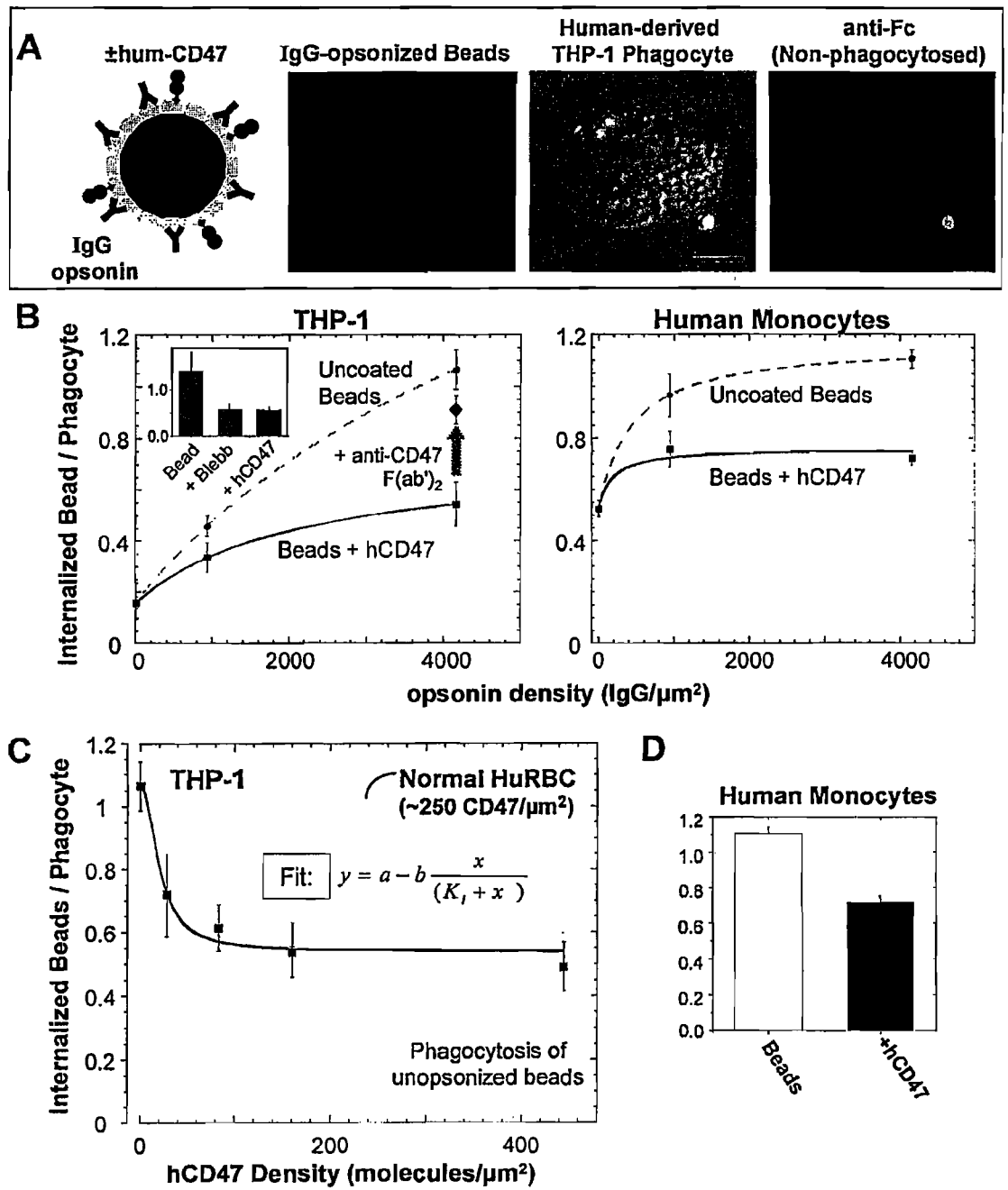

Phagocytosis Assay:

For phagocytosis assays, macrophages were plated in 4 cm², or 2 cm² Lab-Tek II Chambered Coverglass (Nalge Nunc International, Naperville, Ill.) at $1.5 \times 10^5$/cm². Streptavidin polystyrene beads of different radius: 3.5 μm, 1.1 μm, 160 nm (Spherotech) and 100 nm (Ademtech) were added to macrophages at a ratio of 2:1, 20:1, 277:1, and 2206:1 respectively and incubate at 37° C. for 45 min. The ratios were determined based on the surface area of the particles to normalize for particle size differences that resulted in comparable uptake among size ranges tested (FIG. 6). Non-phagocytosed beads were washed with PBS. Cells were fixed with 5% formaldehyde (Fisher Scientific) for 5 minutes, followed by immediate replacement with PBS. For differentiation of non-internalized beads, beads were labeled with a primary antibody, rabbit anti-streptavidin (Sigma) at 1:1000 in PBS for 20 min at 25° C. A second antibody, anti-rabbit R-PE (Sigma) was added at 1:1000 in PBS to the cells and incubated for an additional 20 minutes at 25° C. Cells were then washed with PBS/0.4% BSA and then quantified by light and fluorescent microscopy. At least 200 cells were scored per well and experiments were repeated at least three times.

For stimulated phagocytosis assays, beads with or without CD47 were incubated with rabbit anti-streptavidin as the IgG opsonin. Beads were opsonized at a concentration 1:1000 for 30 min at 25° C. Opsonized beads were washed 2× and resuspended in 50 μl of PBS/0.4% BSA. Phagocytes were washed with PBS and uningested beads were labeled as described above.

For cytoskeletal involvement at the phagocytic synapse, streptavidin beads opsonized with rabbit anti-streptavidin FITC. Opsonized beads of different sizes were added to THP-1 cells, PMA treated and immediately placed at 4° C. for 10 min to synchronize phagocytosis. The temperature of the cells was then immediately increased to 37° C. for 10 min and then fixed with 5% formaldehyde for immunofluorescence. For studies involving blebbistatin (EMD Biosciences), macrophages were treated for 10 min at 4° C. prior to temperature increase to 37° C. or for 45 min and 37° C. Macrophages treated with DMSO were used to verify no solvent effects.

SHP-1 Inhibitor Effect on Phagocytosis:

For phagocytosis assays with CD47 attached particles at 100 nm to 1.1 μm diameter were IgG-opsonizied. THP-1 macrophage, PMA activated were treated with 0-0.5 μM NSC-87877 an SHP-1 Inhibitor (gift from Frank L. Conlon)

5 minutes prior to the addition of IgG-opsonizied particles. Phagocytosis assay occurred at 37° C. for 45 minutes and then fixed for 5 minutes with 5% formaldehyde as described for the phagocytosis assay (Fisher Scientific).

Inhibition of Nano-Scale Particle Uptake:

THP-1 macrophages activated with phorbol 12-myristate 13-acetate (PMA were incubated with chlorpromazine (10 µg/ml in distilled water) or cytochalasin B for 30 min at 37° C. Control cells were incubated with the medium with or without solvent. Followed by incubation with the inhibitors, they were used for uptake studies with IgG-opsonized particles at 37° C. for 45 min.

Lentiviral Transduction:

THP-1 macrophages or A549 cells were transduced with lentivirus overexpressing human CD47 co-expressed with MST-dsRED an RFP analog, or control RFP alone at the indicated MOI in the studies and cells were cultured at $4 \times 10^4$ cells/4 cm$^2$. Lentivirus were incubated briefly for 1 hour with THP-1 or A549 cells at 37° C. and then immediately washed with PBS to remove viral particles and replenished with RPMI 1640 with PMA. THP-1 and A549 were cultured for an addition 3 days at 37° C. and fixed with 5% formaldehyde. Infection of cells tested was monitored by the expression RFP using fluorescent microscopy and random images were taken for quantification. For studies with blebbistatin (EMD Biosciences), both cell types used were pre-incubated 10 minutes prior to the addition of lentiviral particles at 37° C. and blebbistatin was removed followed 1 hour incubation with the viruses.

Quantification of Fluorescent Intensity:

Immunostaining was performed by permeabilization with 0.1% Triton X-100 in PBS for 20 min before blocking for 1 h with 5% BSA in PBS. Staining with primary antibodies was carried out for 1 h at room temperature in PBS. Following washing, samples were incubated with appropriate PE-conjugated secondary antibodies (1:1000). To label cytoskeletal proteins at the phagocytic synapse, primary Ab's prepared with Zenon Alexa 488 or Zenon Alexa 647 Fab labeling kits (Invitrogen) labeled for 45 min at room temperature. Cells were immediately fixed using 5% formaldehyde for 20 minutes and washed with PBS. Samples were analyzed by differential interference contrast (DIC) and fluorescence microscopy.

Post-transduction of lentiviral and expression of RFP, cells were stained with the DNA stain Hoechst (Invitrogen). Random images were taken of phase contrast images along for the 350 nm filter and RFP spectral wavelength 520 nm and quantified using Image J software to determine the number cells and the number of cells expressing RFP.

Images were acquired with an inverted microscope (Olympus; IX71) with a 60× (oil, 1.4 NA) objective using a Cascade CCD camera (Photometrics, Tuscon, Ariz.). Image acquisition was performed with Image Pro software (Media Cybernetics, Silver Spring, Md.). Intensity analysis of the phagocytic synapse was performed using Image J with a 7.7 µm×1.2 µm box. The synapse was aligned at the center of the 7.7 µm length box and the peak intensity designated as the zero in the distance scale on the plots. Fluorescent intensity was normalized by setting the cytoplasmic signal to 1 as the base signal and 5 randomly selected cells were averaged. Student's two-tailed t-tests were performed to assess the significance.

Example 1

CD47 Inhibits Myosin Localization In Phagocytosis

Pseudopod extension and phagocytic cup formation around the target involves extensive remodeling of the actin cytoskeleton. As explained previously, a hallmark of phagocytosis and endocytosis is the actin recruitment to the target cells (Allison et al., 1971, Nat. New Biol. 232(31):153-5; Newman et al., 1991, J. Immunol. 146(3):967-74), but to FcR-mediated phagocytosis, it is the involvement of myosin IIA (Araki, 2006, Front. Biosci. 11:1479-90; Tsai et al., 2008, J. Cell Biol. 180(5):989-1003). When using IgG-opsonized targets of 1.1 µm and 100 nm streptavidin polystyrene particles incubated with human-derived THP-1 macrophages, localization of F-actin to the synapse of the targeted particles was observed. Surprisingly, as shown in FIGS. 11B and 11C, the motor protein non-muscle myosin IIA (NMMIIA) localized during the phagocytosis of both the 1.1 µm particles and the 100 nm particles. As shown in FIGS. 11D and 11E, quantification of these particles near the phagocytic synapse showed a 50% increase in localization of NMMIIA for control IgG-opsonized particles, compared to hCD47 coated particles for both 1.1 µm and 100 nm sizes. This suggests the surprising result that hCD47 reduces myosin IIA localization for not only micro-sized particles, but also for nano-scale particles.

Example 2

CD47 Inhibits Phagocytosis of Nano-scale Particles

In order to assess if CD47 is important in inhibiting FcR-mediated phagocytosis at nano-length scales, the uptake of different-sized streptavidin polystyrene particles having the same physical characteristics was studied to accurately compare the size ranges of interest. The extracellular immunoglobulin-like domains of human CD47 (hCD47) was recombinantly expressed with a spacer domain (Brown et al., 1994, Protein Eng 7(4):515-21; Brown et al., 1998, J. Exp. Med. 188(11): 2083-90) plus a C-terminal biotinylation site. Biotinylation allowed attachment of soluble hCD47 to streptavidin-coated beads of sizes ranging from 100 nm to 3 µm, with densities adjustable to levels previously measured for normal and diseased RBCs (Dahl et al., 2004, Blood 103(3):1131-6; Subramanian et al., 2006, Blood Cells Mol. & Dis. 36(3):364-372).

As shown in FIG. 12, particles were opsonized by pretreatment with anti-streptavidin antibody to induce FcR-mediated phagocytosis (for 45 min at 37° C.), and non-engulfed beads were detected by a second fluorescence. Phagocytosed beads were sterically protected so that the merged DIC and fluorescent images provided a definitive means to quantify the internalized beads per phagocyte. Beads were opsonized at saturating densities of IgG, and over a 20-fold range of CD47 densities, the number of internalized beads per THP-1 was measured. As shown in FIG. 13, particles coated with hCD47 showed comparable levels of IgG-opsonin to uncoated particles confirmed by flow cytometry. As shown in FIGS. 14A and 14B, a reduced level of uptake of the nano-sized particles of 100 and 160 nm was observed with the presence of CD47 by THP-1 macrophages, which was scored based on 200 cells and repeat in triplicate for each density tested. The same trends were observed for the eukaryotic and microbe length scale of 1.1 µm and 3.5 µm sized particles, as shown in FIGS. 14C and 14D. Unopsonized particles with or without hCD47 showed a basal level of uptake by the THP-1 macrophages in the 100 nm to 3.5 µm sizes examined represented by the (grey) horizontal bar. The normal level of CD47 density found on human RBC (Subramanian et al., 2006, Blood 107 (6):2548-2556) was indicated by the vertical bars and humans with certain Rh null phenotypes with reduced levels of CD47 (Mouro-Chanteloup et al., 2003, Blood 101(1):338-344; Arndt et al., 2004, Br. J. Haematol. 125(3):412-4) was indicated by the vertical bars. The minimum number of CD47 inhibition appears to be consistent across a 30-fold particle size range as depicted by the vertical bars. These results showed that even 10-20% of normal CD47 densities are sufficient to inhibit phagocytosis. As shown in Table 1, the minimum number of hCD47 density to inhibit uptake defined as the ($K_i$) was shown to be approximately 20 molecules/$\mu m^2$ for the particle sizes tested.

| Particle Radius | $K_i$ (molecules/$\mu m^2$) |
|---|---|
| 100 nm | 19.9 |
| 160 nm | 13.6 |
| 1.1 $\mu$m | 20* |
| 3.4 $\mu$m | 27.6 |

Example 3

SHP-1 and Myosin Inhibition Effects CD47 Potential

As explained previously, interaction of CD47 on the target and SIRPα on the macrophages leads to a number of downstream processes. This occurs through the receptor-ligation interactions of CD47-SIRPα leading to the phosphorylation SIRPα immunoreceptor tyrosine inhibitory motif (ITIM) (Kharitonenkov et al., 1997, Nature 386(6621):181-6) and subsequent SHP-1 phosphatase induction (Tsuda et al., 1998, J. Biol. Chem. 273(21):13223-9; Veillette et al., 1998, J. Biol. Chem. 273(35):22719-28; Vernon-Wilson et al., 2000, Eur. J. Immunol. 30(8):2130-7). In order to confirm that the interaction of hCD47 coupled to both the nano- and micro-scale streptavidin particles interacts specifically with SIRPα found on THP-1 human macrophages, FACS analysis was performed. As shown in FIG. 15, an antibody against SIRPα known to obstruct hCD47-SIRPα interaction (Subramanian et al., 2006, Blood 107(6):2548-2556) was pre-incubated on THP-1 macrophages that demonstrated soluble hCD47 binds specifically to SIRPα.

Figure 16A:
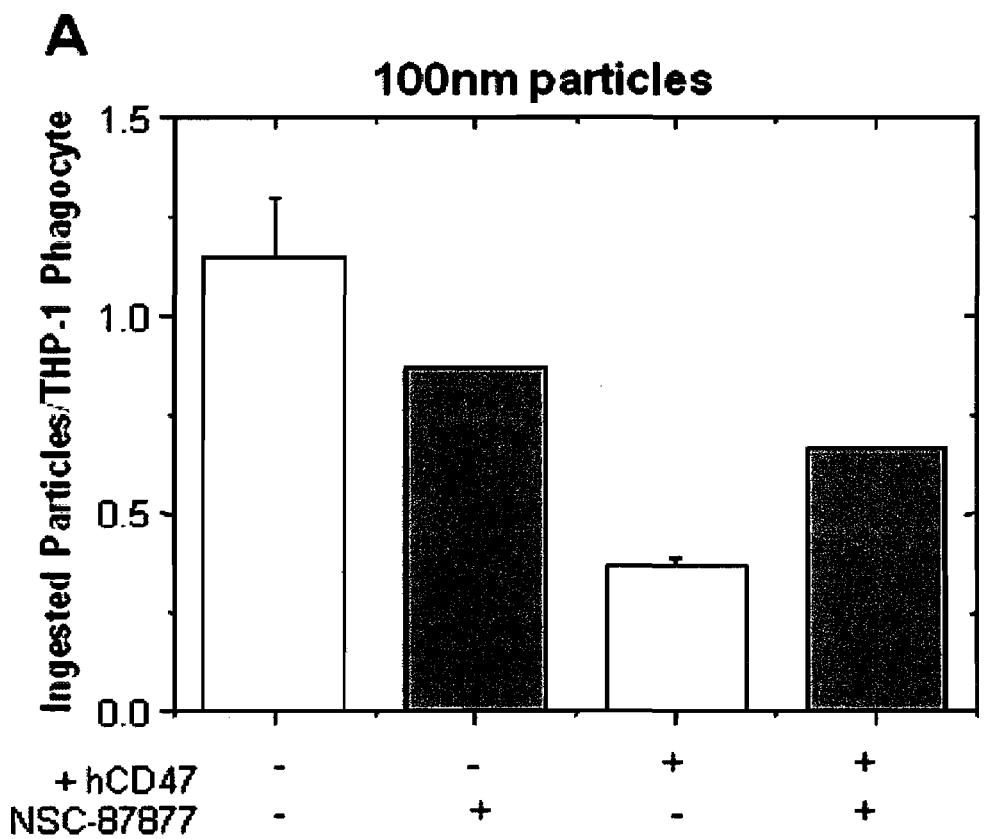
Figure 16A:
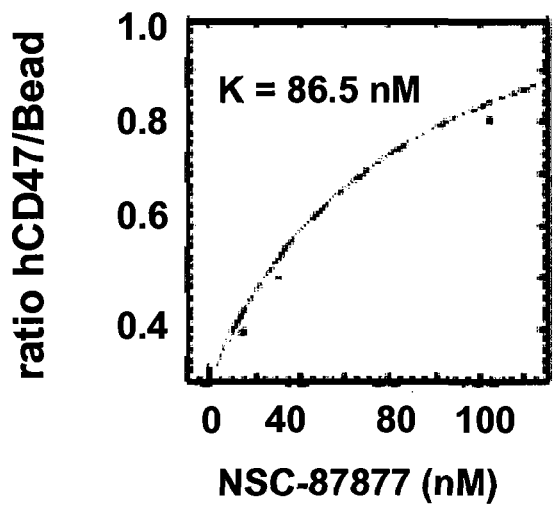
Figure 16B:
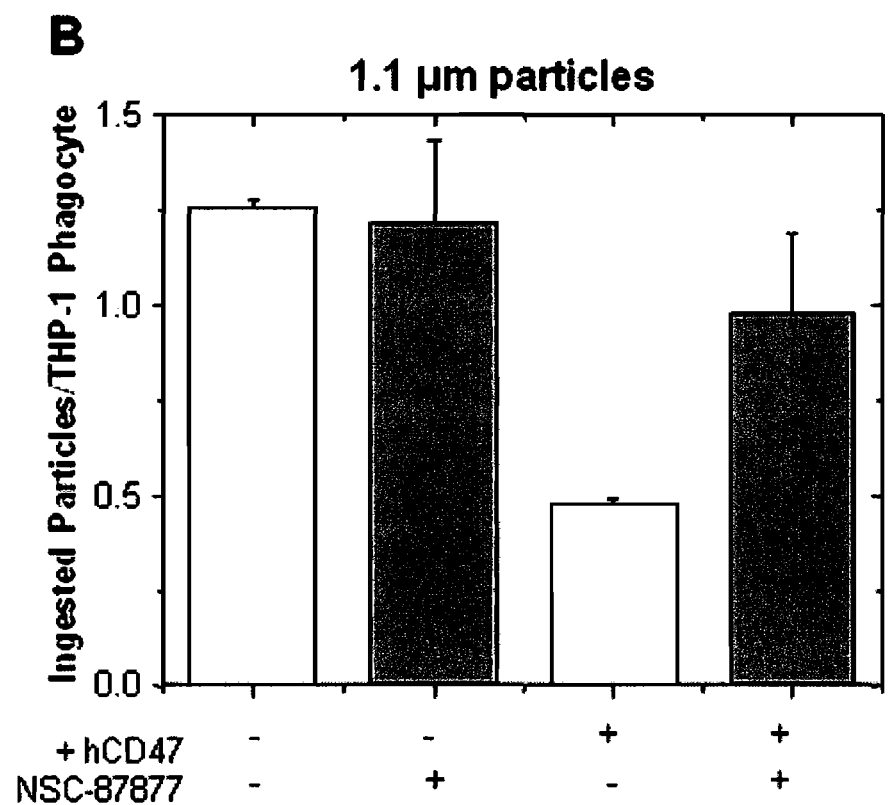

To confirm the correlation between CD47 affect on inhibiting phagocytosis of both nano and micro sized particles, blocked SHP-1 should result in nullifying the CD47 signal. In order to specifically block SHP-1, an inhibitor NSC-87877 was used with a reported high specificity to SHP-1 (Chen et al., 2006, Mol. Pharmacol. 70(2):562-70; Langdon et al., 2007, Development 134(22):4119-30). IgG-opsonized 100 nm streptavidin particles with or without hCD47 was used as targets for THP-1 macrophages treated with or without the SHP-1 inhibitor, NSC-87877 at a concentration of 62.5 nM, which was significantly lower than the reported $IC_{50}$ of 500 nM for SHP-1, to ensure that it was not inhibiting other pathways (Chen et al., 2006, Mol. Pharmacol. 70(2):562-70). The uptake of these particles was measured as the number of particles ingested per phagocyte. As shown in FIG. 16A, beads without hCD47 showed no statistical difference when treated with the SHP-1 inhibitor, but in the case of hCD47 particles, an increase of ingested particles was observed when treated with the SHP-1 inhibitor. Internalization of hCD47 coated beads was plotted as a function of NSC-87877 concentration showed a saturating level of uptake comparable to particles without hCD47. These results for the 1.1 $\mu$m particle targets showed comparable results to 100 nm particles coated with hCD47 resulting in an increase in uptake comparable to uncoated IgG-opsonizied particles, as shown in FIG. 16B. The data for 100 nm and 1.1 $\mu$m sizes are in strong agreement, and show that CD47-SIRPα recruitment of SHP-1 is important for inhibiting uptake of both nano and micron particles.

Figure 16C:
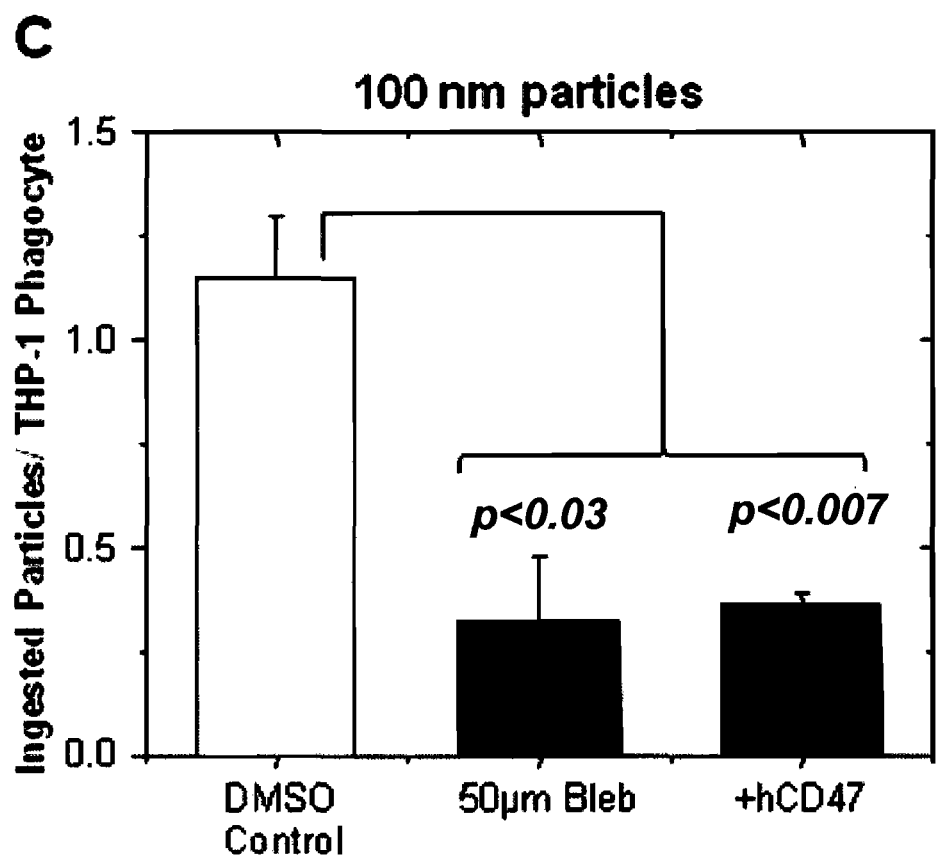
Figure 16D:
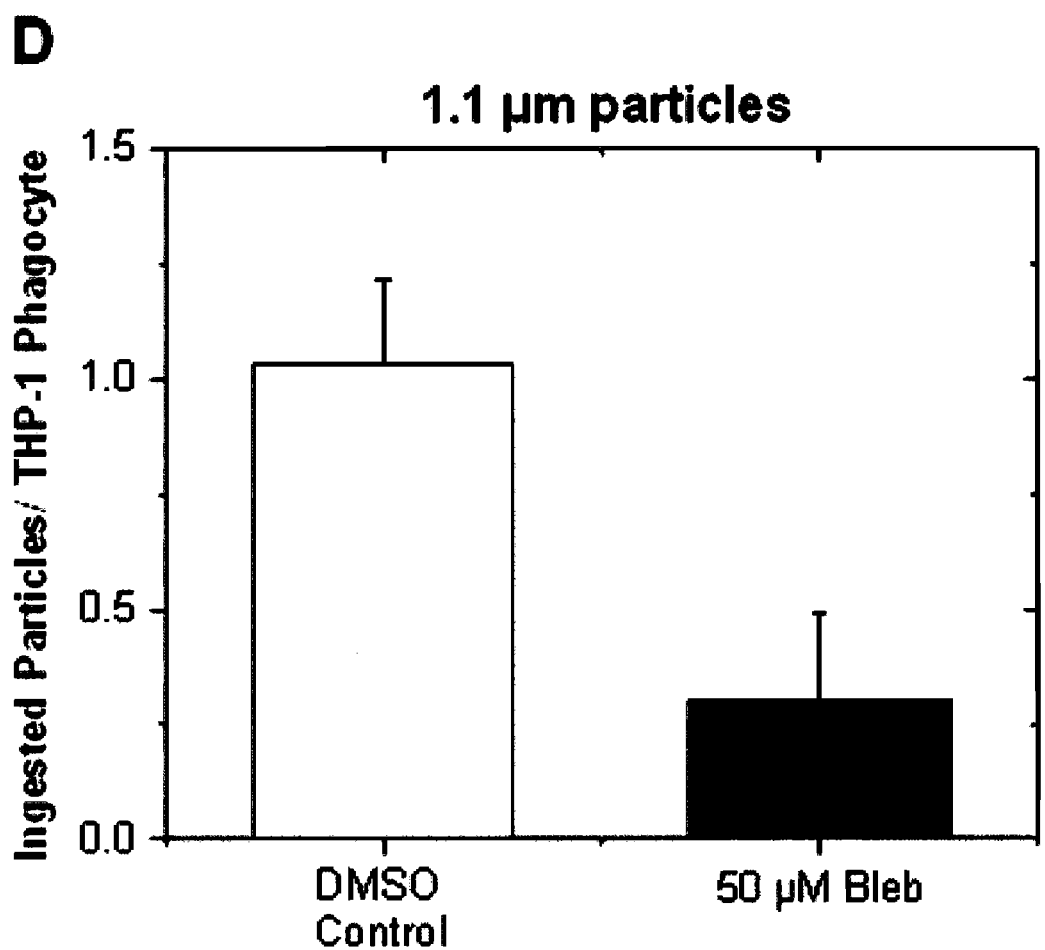

As mentioned previously, macrophages are professional phagocytes that uptake particles through a number of pathways, including phagocytosis and macropinocytosis, that involve the actin cytoskeleton (Swanson et al., 1995, Trends Cell Biol. 5(3):89-93). A unique feature of phagocytosis is the involvement of the motor proteins such as myosins that have been implicated (Mansfield et al., 2000, Blood 95(7):2407-2412). Non-muscle myosin is understood to be expressed in macrophages (Swanson, 1989, J. Cell Sci. 94(Pt 1):135-42), and reports have implicated myosin IIA importance in FcγR-medicated phagocytosis through CD47 deactivation through SHP-1 (Tsai et al., 2008, J. Cell Biol. 180(5):989-1003). It has been speculated that phagocytosis involves a two stage process encompassing myosin as the final step (Araki et al., 1996, J. Cell Biol. 135(5):1249-60; Crowley et al., 1997, J. Exp. Med. 186(7):1027-39; Lowry et al., 1998, J. Exp. Med. 187(2):161-76). To examine the role of myosin, the membrane-permeable drug, blebbistatin, which is an inhibitor of Myosin II ATPase activity (Straight et al., 2003, Science 299(5613):1743-7; Kovacs et al., 2004, J. Biol. Chem. 279 (34):35557-35563), was used to inhibit the uptake of small particles. As shown in FIG. 16C, there was a decrease in uptake of 100 nm IgG-opsonizied particles with THP-1 treated with 50 μM of blebbistatin compared to our DMSO solvent controls, but comparable levels to hCD47 coated particles with untreated THP-1 macrophages. Consistent with the nano-scale particle results, larger 1.1 μm IgG-opsonized particles showed comparable results with blebbistatin treatment (FIG. 16D) that was in agreement with our previous implicating CD47 role in inhibition phagocytosis through myosin IIA (Tsai et al., 2008, J. Cell Biol. 180(5): 989-1003).

Based on the data provided herein, CD47 may be applied to a number of biological applications, including drug delivery carriers with the potential usage of CD47 to disguise foreign particles to disable macrophage engulfment than through the traditional strategies by changing physical properties (Ram et al., 1998, J. Exp. Med. 187(5):743-52; Alcami et al., 2000, Trends Microbiol. 8(9):410-8). A broader implication from a therapeutic prospective, by utilizing CD47 inhibitory effects on macrophages either through a synthetic system may help reduce the level of phagocyte apoptosis as seen in inflammatory diseases (Moghimi et al., 2001, Pharmacol. Rev. 53(2): 283-318; Oliver et al., 2008, Thorax 63(6):519-25).

Example 4

Viral Transduction of Macrophages Decreases with Viral CD47

Regardless of particles size, normal macrophages should be expected to engulf self cells at a lower frequency than typical targets, such as apoptotic and/or foreign cells or particles. The decision of a macrophage to phagocytose is in part made by the extent of target opsonization, which activates assembly of the F-actin cytoskeleton at the phagocytic synapse. However, IgG is high in bodily fluids and certainly binds or adsorbs at some level to all cells (Turrini et al., 1993, Blood 81(11):3146-52), and so activating signals seem unavoidable even to viral particles. For example, lentiviruses, such as visna virus and HIV, have been shown to be taken up by macrophages significantly with antibodies bound to these virus but not when $F(ab)_2$ fragments of the same antibody were used (Robinson et al., 1987, AIDS Res. Hum. Retroviruses 3(3):265-82; Jolly et al., 1989, J. Gen. Virol. 70(Pt 8):2221-6).

In light of the effect of CD47 reducing the level of uptake for 100 nm to 3.5 μm particles (FIG. 14A-D), the effect of CD47 on biologically relevant, nano-size viral particles was examined. Viral particles are also recognized by macrophages and internalized through recognition of these particles by passive IgG-opsonization (Wilflingseder et al., 2007, J. Immunol. 178(12):7840-8). This uptake may have a negative effect since the use of a virus in many cases is to limit the uptake by immune cells to prevent compromising the immune system. A study of myxoma virus 128 L expresses a CD47 homolog suggested that with the absence of this protein result in an increase in activation of monocytes/macrophages cells during infection in rabbits (Cameron et al., 2005, Virology 337(1):55-67). Lentiviral particles are characterized with vesicular stomatitis virus (VSV) g-pseudotype lipid layer with a diameter of 80-100 nm (Greenberg et al., 2007, Invest Opthalmol. Vis. Sci. 48(4):1844-52), which is comparable in size to the synthetic nano-scale particles described herein. A full length human CD47 (hCD47) was expressed with a green fluorescent protein (GFP) at the c-terminus on the viral envelope, with a transient transfection of VSV-g pseudotyped viron packaged with an MST variant of dsRED, that is the least toxic of the red fluorescent protein (RFP), as a reporter for transduction using 293T cell for viral generation (FIG. 17A) (DuBridge et al., 1987, Mol. Cell. Biol. 7(1): 379-87). Fluorescent microscopy images of these lentiviral particles show co-localization of the RFP and GFP signal indicating the presence of CD47 on the lentiviral particles (FIG. 17A, right) and lentiviral particles lacking hCD47 GFP showed no GFP signals (FIG. 18).

To study the uptake of these lentiviral particles with or without hCD47, the lentiviral particles were incubated with THP-1 macrophages (1 hr at 37° C.) at multiplicity of infection (MOI) of 700 (Peranteau et al., 2008, J. Invest. Dermatol. 128(7):1852-60). Viral particles were subsequently removed and replaced with fresh media. After the initial lentiviral particle exposure, THP-1 macrophages were monitored after 72 hours for transduction by DIC and fluorescent microscopy. As depicted in FIG. 17B, fluorescent signals of the control lentiviral particles showed a high level of transduction through RFP signals, while hCD47 lentiviral particles showed a lower level. As depicted in FIG. 17C, quantification of these results showed that control lentivirus had a higher fraction of transduction compared to hCD47 lentivirus with a saturating level of cells transduced with increasing MOI (inset). This was consistent with earlier observations of hCD47 nano-scale particles showing lower levels of uptake (FIGS. 14A and 14B) and reduced the activation of macrophages (FIGS. 16A and 16C). In order to confirm the contributions of hCD47 to the inhibition of transduction in lentiviral particles and to eliminate the possibility that the presence of the additional protein reduces overall transduction, A549 human lung epithelial cells were used, as these cells are not known to express SIRPα (Adams et al., 1998. J. Immunol. 161(4): 1853-9) and the data confirmed by flow cytometry (data not shown), thus eliminating the signaling contributions from CD47-SIRPα ligation. Lentiviral particles were incubated with A549 with an MOI of 270 with the same treatment as described for THP-1 macrophages; leading to an increase in the level of RFP expression with hCD47 lentiviral particles (FIG. 17D). As depicted in FIG. 17E, the quantified results from randomly selected images showed that levels of transduction were higher with hCD47 as compared to controls with a dose dependent response and a divergence of transduction with higher MOI. This suggests that CD47 signals inhibition in cells expressing SIRPα, but in the absence of this receptor-ligand, interaction in non-professional phagocytes may lead to a synergistic effect when associated with other proteins.

Example 5

To examine the role of Myosin IIA in lentiviral transduction and the role of CD47 reducing uptake, macrophages were incubated with blebbistatin, a specific inhibitor of myosin IIA (Kovacs et al., 2004, J. Biol. Chem. 279(34):35557-35563). As depicted in FIG. 19A, blebbistatin inhibited transduction of the lentiviral particles, but no changes were observed for overexpressed hCD47 lentiviral particles. The blebbistatin-treated macrophages with overexpressed hCD47 and control lentiviral particles showed a similar level of transduction, suggesting a common pathway observed in micron sized targets may apply to nano-scale particles and virus (FIGS. 16 and 17). As depicted in FIG. 19B, blebbistatin treatment of THP-1 macrophages showed a dose dependent response in transduction efficiency of control lentivirus. In contrast to this, FIG. 20 shows blebbistatin had no effect on lentivirus transduction in A549 cells, suggesting the role of CD47 in inhibiting myosin II (Tsai et al., 2008, J. Cell Biol. 180(5): 989-1003).

Based on the data provided herein, CD47 may be applied to a number of biological applications, including drug delivery carriers with the potential usage of CD47 to disguise foreign particles to disable macrophage engulfment than through the traditional strategies by changing physical properties (Ram et al., 1998, J. Exp. Med. 187(5):743-52; Alcami et al., 2000, Trends Microbiol. 8(9):410-8). A broader implication from a therapeutic prospective, by utilizing CD47 inhibitory effects on macrophages either through a synthetic or viral system may help reduce the level of phagocyte apoptosis as seen in inflammatory diseases (Moghimi et al., 2001, Pharmacol. Rev 53(2):283-318; Oliver et al., 2008, Thorax 63(6):519-25).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A composition comprising:
   - a viral particle having a radius of less than about 400 nm; and,
   - at least one peptide comprising SEQ ID NO:2,
   - wherein said at least one peptide is expressed on an exposed surface of said viral particle.

2. The composition of claim 1, wherein said particle has a radius of less than about 150 nm.

3. The composition of claim 1, wherein said particle comprises a lipid coat.

4. The composition of claim 3, wherein said particle is a lentivirus.

5. The composition of claim 1, wherein the amount of said peptide comprising SEQ ID NO:2 in said viral particle is between about 20 and about 250 molecules/μm².

6. A pharmaceutical composition comprising:
   - a viral particle having a radius of less than about 400 nm; and,
   - at least one peptide comprising SEQ ID NO:2,
   - wherein said at least one peptide is expressed on an exposed surface of said viral particle; and,
   - a pharmaceutically acceptable carrier.

7. A method of preparing a viral particle that evades phagocytosis by a phagocytic cell, said method comprising expressing at least one peptide comprising SEQ ID NO:2 on an exposed surface of said viral particle, whereby said viral particle evades phagocytosis by said phagocytic cell when said viral particle is exposed to said phagocytic cell.

8. A method of increasing the life of a viral particle in vivo in a mammal, said method comprising expressing at least one peptide comprising SEQ ID NO:2 on an exposed surface of said viral particle and administering said viral particle having at least one peptide comprising SEQ ID NO:2 expressed to said mammal,
   wherein said administered viral particle has a longer half life in said mammal than an otherwise identical viral particle that does not have at least one peptide comprising SEQ ID NO:2 expressed thereon.

9. The method of claim 8, wherein said viral particle has a radius of less than about 400 nm.

10. The method of claim 9, wherein said viral particle has a radius of less than about 150 nm.

11. The method of claim 8, wherein said viral particle comprises a lipid coat.

12. The method of claim 11, wherein said viral particle is a lentivirus.

13. The method of claim 8, wherein the amount of said peptide comprising SEQ ID NO:2 in said viral particle is between about 20 and about 250 molecules/μm².

14. The method of claim 8, wherein said at least one peptide comprising SEQ ID NO:2 is human CD47.

* * * * *

SEQUENCE LISTING

<160> NUMBER OF SEQ ID NOS: 2

<210> SEQ ID NO 1
<211> LENGTH: 305
<212> TYPE: PRT
<213> ORGANISM: Homo sapiens

<400> SEQUENCE: 1

Met Trp Pro Leu Val Ala Ala Leu Leu Leu Gly Ser Ala Cys Cys Gly

```
                1               5                      10                      15
        Ser Ala Gln Leu Leu Phe Asn Lys Thr Lys Ser Val Glu Phe Thr Phe
                        20                      25                      30

Cys Asn Asp Thr Val Val Ile Pro Cys Phe Val Thr Asn Met Glu Ala
                        35                      40                      45

Gln Asn Thr Thr Glu Val Tyr Val Lys Trp Lys Phe Lys Gly Arg Asp
                50                      55                      60

Ile Tyr Thr Phe Asp Gly Ala Leu Asn Lys Ser Thr Val Pro Thr Asp
        65                      70                      75                      80

Phe Ser Ser Ala Lys Ile Glu Val Ser Gln Leu Leu Lys Gly Asp Ala
                        85                      90                      95

Ser Leu Lys Met Asp Lys Ser Asp Ala Val Ser His Thr Gly Asn Tyr
                        100                     105                     110

Thr Cys Glu Val Thr Glu Leu Thr Arg Glu Gly Glu Thr Ile Ile Glu
                        115                     120                     125

Leu Lys Tyr Arg Val Val Ser Trp Phe Ser Pro Asn Glu Asn Ile Leu
                130                     135                     140

Ile Val Ile Phe Pro Ile Phe Ala Ile Leu Leu Phe Trp Gly Gln Phe
        145                     150                     155                     160

Gly Ile Lys Thr Leu Lys Tyr Arg Ser Gly Gly Met Asp Glu Lys Thr
                        165                     170                     175

Ile Ala Leu Leu Val Ala Gly Leu Val Ile Thr Val Ile Val Ile Val
                        180                     185                     190

Gly Ala Ile Leu Phe Val Pro Gly Glu Tyr Ser Leu Lys Asn Ala Thr
                        195                     200                     205

Gly Leu Gly Leu Ile Val Thr Ser Thr Gly Ile Leu Ile Leu Leu His
                210                     215                     220

Tyr Tyr Val Phe Ser Thr Ala Ile Gly Leu Thr Ser Phe Val Ile Ala
        225                     230                     235                     240

Ile Leu Val Ile Gln Val Ile Ala Tyr Ile Leu Ala Val Val Gly Leu
                        245                     250                     255

Ser Leu Cys Ile Ala Ala Cys Ile Pro Met His Gly Pro Leu Leu Ile
                        260                     265                     270

Ser Gly Leu Ser Ile Leu Ala Leu Ala Gln Leu Leu Gly Leu Val Tyr
                        275                     280                     285

Met Lys Phe Val Ala Ser Asn Gln Lys Thr Ile Gln Pro Pro Arg Asn
                290                     295                     300

Asn
        305

<210> SEQ ID NO 2
<211> LENGTH: 140
<212> TYPE: PRT
<213> ORGANISM: Homo sapiens

<400> SEQUENCE: 2

Met Trp Pro Leu Val Ala Ala Leu Leu Leu Gly Ser Ala Cys Cys Gly
        1                       5                       10                      15

Ser Ala Gln Leu Leu Phe Asn Lys Thr Lys Ser Val Glu Phe Thr Phe
                        20                      25                      30

Cys Asn Asp Thr Val Val Ile Pro Cys Phe Val Thr Asn Met Glu Ala
                        35                      40                      45

Gln Asn Thr Thr Glu Val Tyr Val Lys Trp Lys Phe Lys Gly Arg Asp
                50                      55                      60
```

```
Ile Tyr Thr Phe Asp Gly Ala Leu Asn Lys Ser Thr Val Pro Thr Asp
 65              70                  75                  80

Phe Ser Ser Ala Lys Ile Glu Val Ser Gln Leu Leu Lys Gly Asp Ala
             85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn
        130                 135                 140
```